(12) United States Patent
Rockrohr et al.

(10) Patent No.: US 12,207,894 B2
(45) Date of Patent: Jan. 28, 2025

(54) ENERGY DISCONNECT FOR ROBOTIC SURGICAL ASSEMBLIES

(71) Applicant: Covidien LP, Mansfield, MA (US)

(72) Inventors: Brian Rockrohr, Guilford, CT (US); Jaimeen Kapadia, Cambridge, MA (US); Eric Taylor, Southington, CT (US)

(73) Assignee: Covidien LP, Mansfield, MA (US)

( * ) Notice: Subject to any disclaimer, the term of this patent is extended or adjusted under 35 U.S.C. 154(b) by 1118 days.

(21) Appl. No.: 16/643,646

(22) PCT Filed: Sep. 6, 2018

(86) PCT No.: PCT/US2018/049632
§ 371 (c)(1),
(2) Date: Mar. 2, 2020

(87) PCT Pub. No.: WO2019/051004
PCT Pub. Date: Mar. 14, 2019

(65) Prior Publication Data
US 2020/0237460 A1    Jul. 30, 2020

Related U.S. Application Data

(60) Provisional application No. 62/555,936, filed on Sep. 8, 2017.

(51) Int. Cl.
*A61B 18/12* (2006.01)
*A61B 34/30* (2016.01)
(Continued)

(52) U.S. Cl.
CPC .............. *A61B 34/37* (2016.02); *A61B 34/30* (2016.02); *A61B 34/32* (2016.02); *A61B 34/35* (2016.02); *A61B 46/10* (2016.02)

(58) Field of Classification Search
CPC .......... A61B 34/30; A61B 34/32; A61B 34/35; A61B 34/37; A61B 2034/305
See application file for complete search history.

(56) References Cited

U.S. PATENT DOCUMENTS 2,957,353 A    10/1960    Babacz
3,111,328 A    11/1963    Di Rito et al.
(Continued)

FOREIGN PATENT DOCUMENTS

CA    2451558 A1    1/2003
CN    1547454 A    11/2004
(Continued)

OTHER PUBLICATIONS

India Examination Report for application No. 202017009147 dated May 5, 2022 with English translation.
(Continued)

*Primary Examiner* — Daniel W Fowler
(74) *Attorney, Agent, or Firm* — Carter, DeLuca & Farrell LLP

(57) ABSTRACT

A robotic surgical system includes an electrosurgical energy source, an instrument drive unit, a sterile interface module coupled to the instrument drive unit, and a robotic surgical instrument selectively couplable to the sterile interface module. The robotic surgical instrument may be disposed in electrical communication with the electrosurgical energy source while the robotic surgical instrument is coupled to the sterile interface module. The robotic surgical instrument is configured to automatically electrically disconnect from the electrosurgical energy source when the robotic surgical instrument is uncoupled from the sterile interface module.

16 Claims, 6 Drawing Sheets

(51) Int. Cl.
  *A61B 34/32* (2016.01)
  *A61B 34/35* (2016.01)
  *A61B 34/37* (2016.01)
  *A61B 46/10* (2016.01)

(56) References Cited

U.S. PATENT DOCUMENTS

| | | |
|---|---|---|
| 3,695,058 A | 10/1972 | Keith, Jr. |
| 3,734,515 A | 5/1973 | Dudek |
| 3,759,336 A | 9/1973 | Marcovitz et al. |
| 4,162,399 A | 7/1979 | Hudson |
| 4,606,343 A | 8/1986 | Conta et al. |
| 4,683,772 A | 8/1987 | Colimitra |
| 4,705,038 A | 11/1987 | Sjostrom et al. |
| 4,722,685 A | 2/1988 | de Estrada et al. |
| 4,823,807 A | 4/1989 | Russell et al. |
| 4,862,759 A | 9/1989 | Trevelyan et al. |
| 4,874,181 A | 10/1989 | Hsu |
| 5,129,118 A | 7/1992 | Walmesley |
| 5,129,570 A | 7/1992 | Schulze et al. |
| 5,152,744 A | 10/1992 | Krause et al. |
| 5,301,061 A | 4/1994 | Nakada et al. |
| 5,312,023 A | 5/1994 | Green et al. |
| 5,326,013 A | 7/1994 | Green et al. |
| 5,349,344 A * | 9/1994 | Head .......... G05B 19/042 341/26 |
| 5,350,355 A | 9/1994 | Sklar |
| 5,383,874 A | 1/1995 | Jackson et al. |
| 5,383,880 A | 1/1995 | Hooven |
| 5,389,098 A | 2/1995 | Tsuruta et al. |
| 5,395,033 A | 3/1995 | Byrne et al. |
| 5,400,267 A | 3/1995 | Denen et al. |
| 5,411,508 A | 5/1995 | Bessler et al. |
| 5,413,267 A | 5/1995 | Solyntjes et al. |
| 5,427,087 A | 6/1995 | Ito et al. |
| 5,433,721 A | 7/1995 | Hooven et al. |
| 5,443,462 A * | 8/1995 | Hannant .......... B23K 9/29 606/41 |
| 5,467,911 A | 11/1995 | Tsuruta et al. |
| 5,476,379 A | 12/1995 | Disel |
| 5,487,499 A | 1/1996 | Sorrentino et al. |
| 5,512,025 A * | 4/1996 | Dalebout .......... A63B 71/0622 482/902 |
| 5,518,163 A | 5/1996 | Hooven |
| 5,518,164 A | 5/1996 | Hooven |
| 5,526,822 A | 6/1996 | Burbank et al. |
| 5,529,235 A | 6/1996 | Boiarski et al. |
| 5,535,934 A | 7/1996 | Boiarski et al. |
| 5,535,937 A | 7/1996 | Boiarski et al. |
| 5,540,375 A | 7/1996 | Bolanos et al. |
| 5,540,706 A | 7/1996 | Aust et al. |
| 5,542,594 A | 8/1996 | McKean et al. |
| 5,549,637 A | 8/1996 | Crainich |
| 5,553,675 A | 9/1996 | Pitzen et al. |
| 5,562,239 A | 10/1996 | Boiarski et al. |
| 5,564,615 A | 10/1996 | Bishop et al. |
| 5,609,560 A | 3/1997 | Ichikawa et al. |
| 5,617,857 A * | 4/1997 | Chader .......... A61B 5/064 600/475 |
| 5,626,587 A | 5/1997 | Bishop et al. |
| 5,632,432 A | 5/1997 | Schulze et al. |
| 5,645,209 A | 7/1997 | Green et al. |
| 5,647,526 A | 7/1997 | Green et al. |
| 5,653,374 A | 8/1997 | Young et al. |
| 5,658,300 A | 8/1997 | Bito et al. |
| 5,662,662 A | 9/1997 | Bishop et al. |
| 5,667,517 A | 9/1997 | Hooven |
| 5,693,042 A | 12/1997 | Boiarski et al. |
| 5,704,534 A | 1/1998 | Huitema et al. |
| 5,713,505 A | 2/1998 | Huitema |
| 5,762,603 A | 6/1998 | Thompson |
| 5,779,130 A | 7/1998 | Alesi et al. |
| 5,782,396 A | 7/1998 | Mastri et al. |
| 5,782,397 A | 7/1998 | Koukline |
| 5,784,542 A | 7/1998 | Ohm et al. |
| 5,792,573 A | 8/1998 | Pitzen et al. |
| 5,797,536 A | 8/1998 | Smith et al. |
| 5,797,900 A | 8/1998 | Madhani et al. |
| 5,820,009 A | 10/1998 | Melling et al. |
| 5,863,159 A | 1/1999 | Lasko |
| 5,908,427 A | 6/1999 | McKean et al. |
| 5,954,259 A | 9/1999 | Viola et al. |
| 5,964,774 A | 10/1999 | McKean et al. |
| 5,993,454 A | 11/1999 | Longo |
| 6,009,540 A * | 12/1999 | Craft .......... G06F 11/2284 713/400 |
| 6,010,054 A | 1/2000 | Johnson et al. |
| 6,017,354 A | 1/2000 | Culp et al. |
| 6,032,849 A | 3/2000 | Mastri et al. |
| 6,045,560 A | 4/2000 | McKean et al. |
| 6,090,123 A | 7/2000 | Culp et al. |
| 6,126,651 A | 10/2000 | Mayer |
| 6,129,547 A | 10/2000 | Cise et al. |
| 6,132,368 A | 10/2000 | Cooper |
| 6,165,169 A | 12/2000 | Panescu et al. |
| 6,206,903 B1 | 3/2001 | Ramans |
| 6,239,732 B1 | 5/2001 | Cusey |
| 6,241,139 B1 | 6/2001 | Milliman et al. |
| 6,246,200 B1 | 6/2001 | Blumenkranz et al. |
| 6,264,086 B1 | 7/2001 | McGuckin, Jr. |
| 6,264,087 B1 | 7/2001 | Whitman |
| 6,302,311 B1 | 10/2001 | Adams et al. |
| 6,312,435 B1 | 11/2001 | Wallace et al. |
| 6,315,184 B1 | 11/2001 | Whitman |
| 6,321,855 B1 | 11/2001 | Barnes |
| 6,329,778 B1 | 12/2001 | Culp et al. |
| 6,331,181 B1 | 12/2001 | Tierney et al. |
| 6,343,731 B1 | 2/2002 | Adams et al. |
| 6,348,061 B1 | 2/2002 | Whitman |
| 6,368,324 B1 | 4/2002 | Dinger et al. |
| 6,371,909 B1 | 4/2002 | Hoeg et al. |
| 6,394,998 B1 | 5/2002 | Wallace et al. |
| 6,424,885 B1 | 7/2002 | Niemeyer et al. |
| 6,434,507 B1 | 8/2002 | Clayton et al. |
| 6,441,577 B2 | 8/2002 | Blumenkranz et al. |
| 6,443,973 B1 | 9/2002 | Whitman |
| 6,451,027 B1 | 9/2002 | Cooper et al. |
| 6,459,926 B1 | 10/2002 | Nowlin et al. |
| 6,461,372 B1 | 10/2002 | Jensen et al. |
| 6,488,197 B1 | 12/2002 | Whitman |
| 6,491,201 B1 | 12/2002 | Whitman |
| 6,491,691 B1 | 12/2002 | Morley et al. |
| 6,491,701 B2 | 12/2002 | Tierney et al. |
| 6,493,608 B1 | 12/2002 | Niemeyer |
| 6,533,157 B1 | 3/2003 | Whitman |
| 6,537,280 B2 | 3/2003 | Dinger et al. |
| 6,554,844 B2 | 4/2003 | Lee et al. |
| 6,565,554 B1 | 5/2003 | Niemeyer |
| 6,567,695 B1 * | 5/2003 | Gruzdowich .......... A61N 1/0408 607/2 |
| 6,610,066 B2 | 8/2003 | Dinger et al. |
| 6,611,793 B1 | 8/2003 | Burnside et al. |
| 6,645,196 B1 | 11/2003 | Nixon et al. |
| 6,645,218 B1 | 11/2003 | Cassidy et al. |
| 6,654,999 B2 | 12/2003 | Stoddard et al. |
| 6,659,939 B2 | 12/2003 | Moll et al. |
| 6,671,581 B2 | 12/2003 | Niemeyer et al. |
| 6,676,684 B1 | 1/2004 | Morley et al. |
| 6,685,698 B2 | 2/2004 | Morley et al. |
| 6,698,643 B2 | 3/2004 | Whitman |
| 6,699,177 B1 | 3/2004 | Wang et al. |
| 6,699,235 B2 | 3/2004 | Wallace et al. |
| 6,714,839 B2 | 3/2004 | Salisbury, Jr. et al. |
| 6,716,233 B1 | 4/2004 | Whitman |
| 6,728,599 B2 | 4/2004 | Wang et al. |
| 6,743,240 B2 | 6/2004 | Smith et al. |
| 6,746,443 B1 | 6/2004 | Morley et al. |
| 6,766,204 B2 | 7/2004 | Niemeyer et al. |
| 6,770,081 B1 | 8/2004 | Cooper et al. |
| 6,772,053 B2 | 8/2004 | Niemeyer |
| 6,783,524 B2 | 8/2004 | Anderson et al. |
| 6,783,533 B2 | 8/2004 | Green et al. |
| 6,792,390 B1 | 9/2004 | Burnside et al. |
| 6,793,652 B1 | 9/2004 | Whitman et al. |

(56) References Cited

U.S. PATENT DOCUMENTS

| | | |
|---|---|---|
| 6,793,653 B2 | 9/2004 | Sanchez et al. |
| 6,799,065 B1 | 9/2004 | Niemeyer |
| 6,817,508 B1 | 11/2004 | Racenet et al. |
| 6,830,174 B2 | 12/2004 | Hillstead et al. |
| 6,837,883 B2 | 1/2005 | Moll et al. |
| 6,839,612 B2 | 1/2005 | Sanchez et al. |
| 6,840,938 B1 | 1/2005 | Morley et al. |
| 6,843,403 B2 | 1/2005 | Whitman |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,860,892 B1 | 3/2005 | Tanaka et al. |
| 6,866,671 B2 | 3/2005 | Tierney et al. |
| 6,871,117 B2 | 3/2005 | Wang et al. |
| 6,879,880 B2 | 4/2005 | Nowlin et al. |
| 6,899,538 B2 | 5/2005 | Matoba |
| 6,899,705 B2 | 5/2005 | Niemeyer |
| 6,902,560 B1 | 6/2005 | Morley et al. |
| 6,905,057 B2 | 6/2005 | Swayze et al. |
| 6,936,042 B2 | 8/2005 | Wallace et al. |
| 6,951,535 B2 | 10/2005 | Ghodoussi et al. |
| 6,959,852 B2 | 11/2005 | Shelton, IV et al. |
| 6,964,363 B2 | 11/2005 | Wales et al. |
| 6,974,449 B2 | 12/2005 | Niemeyer |
| 6,981,628 B2 | 1/2006 | Wales |
| 6,981,941 B2 | 1/2006 | Whitman et al. |
| 6,986,451 B1 | 1/2006 | Mastri et al. |
| 6,988,649 B2 | 1/2006 | Shelton, IV et al. |
| 6,991,627 B2 | 1/2006 | Madhani et al. |
| 6,994,708 B2 | 2/2006 | Manzo |
| 7,032,798 B2 | 4/2006 | Whitman et al. |
| 7,048,745 B2 | 5/2006 | Tierney et al. |
| RE39,152 E | 6/2006 | Aust et al. |
| 7,055,731 B2 | 6/2006 | Shelton, IV et al. |
| 7,059,508 B2 | 6/2006 | Shelton, IV et al. |
| 7,066,926 B2 | 6/2006 | Wallace et al. |
| 7,077,856 B2 | 7/2006 | Whitman |
| 7,111,769 B2 | 9/2006 | Wales et al. |
| 7,118,582 B1 | 10/2006 | Wang et al. |
| 7,122,029 B2 | 10/2006 | Koop et al. |
| 7,125,403 B2 | 10/2006 | Julian et al. |
| 7,140,528 B2 | 11/2006 | Shelton, IV |
| 7,141,049 B2 | 11/2006 | Stern et al. |
| 7,143,923 B2 | 12/2006 | Shelton, IV et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,155,315 B2 | 12/2006 | Niemeyer et al. |
| 7,172,104 B2 | 2/2007 | Scirica et al. |
| 7,225,964 B2 | 6/2007 | Mastri et al. |
| 7,238,021 B1 | 7/2007 | Johnson |
| 7,239,940 B2 | 7/2007 | Wang et al. |
| 7,246,734 B2 | 7/2007 | Shelton, IV |
| 7,252,660 B2 | 8/2007 | Kunz |
| 7,306,597 B2 | 12/2007 | Manzo |
| 7,328,828 B2 | 2/2008 | Ortiz et al. |
| 7,357,774 B2 | 4/2008 | Cooper |
| 7,364,061 B2 | 4/2008 | Swayze et al. |
| 7,373,219 B2 | 5/2008 | Nowlin et al. |
| 7,379,790 B2 | 5/2008 | Toth et al. |
| 7,380,695 B2 | 6/2008 | Doll et al. |
| 7,380,696 B2 | 6/2008 | Shelton, IV et al. |
| 7,386,365 B2 | 6/2008 | Nixon |
| 7,391,173 B2 | 6/2008 | Schena |
| 7,398,707 B2 | 7/2008 | Morley et al. |
| 7,404,508 B2 | 7/2008 | Smith et al. |
| 7,407,078 B2 | 8/2008 | Shelton, IV et al. |
| 7,413,565 B2 | 8/2008 | Wang et al. |
| 7,416,101 B2 | 8/2008 | Shelton, IV et al. |
| 7,419,080 B2 | 9/2008 | Smith et al. |
| 7,422,139 B2 | 9/2008 | Shelton, IV et al. |
| 7,422,592 B2 | 9/2008 | Morley et al. |
| 7,431,189 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,453,227 B2 | 11/2008 | Prisco et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,347 B2 | 1/2009 | Roy |
| 7,481,824 B2 | 1/2009 | Boudreaux et al. |
| 7,487,899 B2 | 2/2009 | Shelton, IV et al. |
| 7,524,320 B2 | 4/2009 | Tierney et al. |
| 7,549,564 B2 | 6/2009 | Boudreaux |
| 7,565,993 B2 | 7/2009 | Milliman et al. |
| 7,568,603 B2 | 8/2009 | Shelton, IV et al. |
| 7,574,250 B2 | 8/2009 | Niemeyer |
| 7,575,144 B2 | 8/2009 | Ortiz et al. |
| 7,588,175 B2 | 9/2009 | Timm et al. |
| 7,588,176 B2 | 9/2009 | Timm et al. |
| 7,594,912 B2 | 9/2009 | Cooper et al. |
| 7,607,440 B2 | 10/2009 | Coste-Maniere et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,666,191 B2 | 2/2010 | Orban, III et al. |
| 7,670,334 B2 | 3/2010 | Hueil et al. |
| 7,673,780 B2 | 3/2010 | Shelton, IV et al. |
| 7,682,357 B2 | 3/2010 | Ghodoussi et al. |
| 7,689,320 B2 | 3/2010 | Prisco et al. |
| 7,695,481 B2 | 4/2010 | Wang et al. |
| 7,695,485 B2 | 4/2010 | Whitman et al. |
| 7,699,835 B2 | 4/2010 | Lee et al. |
| 7,699,855 B2 | 4/2010 | Anderson et al. |
| 7,713,263 B2 | 5/2010 | Niemeyer |
| 7,721,931 B2 | 5/2010 | Shelton, IV et al. |
| 7,725,214 B2 | 5/2010 | Diolaiti |
| 7,727,244 B2 | 6/2010 | Orban, III et al. |
| 7,738,971 B2 | 6/2010 | Swayze et al. |
| 7,740,159 B2 | 6/2010 | Shelton, IV et al. |
| 7,741,802 B2 | 6/2010 | Prisco et al. |
| 7,743,960 B2 | 6/2010 | Whitman et al. |
| 7,756,036 B2 | 7/2010 | Druke et al. |
| 7,757,028 B2 | 7/2010 | Druke et al. |
| 7,758,613 B2 | 7/2010 | Whitman |
| 7,762,825 B2 | 7/2010 | Burbank et al. |
| 7,766,210 B2 | 8/2010 | Shelton, IV et al. |
| 7,770,773 B2 | 8/2010 | Whitman et al. |
| 7,770,775 B2 | 8/2010 | Shelton, IV et al. |
| 7,778,733 B2 | 8/2010 | Nowlin et al. |
| 7,793,812 B2 | 9/2010 | Moore et al. |
| 7,799,039 B2 | 9/2010 | Shelton, IV et al. |
| 7,802,712 B2 | 9/2010 | Milliman et al. |
| 7,803,151 B2 | 9/2010 | Whitman |
| 7,806,891 B2 | 10/2010 | Nowlin et al. |
| 7,819,859 B2 | 10/2010 | Prisco et al. |
| 7,819,885 B2 | 10/2010 | Cooper |
| 7,822,458 B2 | 10/2010 | Webster, III et al. |
| 7,824,401 B2 | 11/2010 | Manzo et al. |
| 7,835,823 B2 | 11/2010 | Sillman et al. |
| 7,843,158 B2 | 11/2010 | Prisco |
| 7,845,534 B2 | 12/2010 | Viola et al. |
| 7,845,537 B2 | 12/2010 | Shelton, IV et al. |
| 7,857,185 B2 | 12/2010 | Swayze et al. |
| 7,865,266 B2 | 1/2011 | Moll et al. |
| 7,865,269 B2 | 1/2011 | Prisco et al. |
| 7,870,989 B2 | 1/2011 | Viola et al. |
| 7,886,743 B2 | 2/2011 | Cooper et al. |
| 7,899,578 B2 | 3/2011 | Prisco et al. |
| 7,900,805 B2 | 3/2011 | Shelton, IV et al. |
| 7,905,897 B2 | 3/2011 | Whitman et al. |
| 7,907,166 B2 | 3/2011 | Lamprecht et al. |
| 7,918,230 B2 | 4/2011 | Whitman et al. |
| 7,922,061 B2 | 4/2011 | Shelton, IV et al. |
| 7,922,719 B2 | 4/2011 | Ralph et al. |
| 7,935,130 B2 | 5/2011 | Williams |
| 7,947,034 B2 | 5/2011 | Whitman |
| 7,951,071 B2 | 5/2011 | Whitman et al. |
| 7,954,682 B2 | 6/2011 | Giordano et al. |
| 7,959,051 B2 | 6/2011 | Smith et al. |
| 7,963,433 B2 | 6/2011 | Whitman et al. |
| 7,963,913 B2 | 6/2011 | Devengenzo et al. |
| 7,967,178 B2 | 6/2011 | Scirica et al. |
| 7,967,179 B2 | 6/2011 | Olson et al. |

(56) References Cited

U.S. PATENT DOCUMENTS

| | | |
|---|---|---|
| 7,983,793 B2 | 7/2011 | Toth et al. |
| 7,992,758 B2 | 8/2011 | Whitman et al. |
| 8,002,767 B2 | 8/2011 | Sanchez et al. |
| 8,004,229 B2 | 8/2011 | Nowlin et al. |
| 8,011,550 B2 | 9/2011 | Aranyi et al. |
| 8,012,170 B2 | 9/2011 | Whitman et al. |
| 8,016,178 B2 | 9/2011 | Olson et al. |
| 8,016,855 B2 | 9/2011 | Whitman et al. |
| 8,020,743 B2 | 9/2011 | Shelton, IV |
| 8,025,199 B2 | 9/2011 | Whitman et al. |
| 8,035,487 B2 | 10/2011 | Malackowski |
| 8,052,024 B2 | 11/2011 | Viola et al. |
| 8,054,752 B2 | 11/2011 | Druke et al. |
| 8,062,288 B2 | 11/2011 | Cooper et al. |
| 8,074,859 B2 | 12/2011 | Kostrzewski |
| 8,079,950 B2 | 12/2011 | Stern et al. |
| 8,092,451 B2 | 1/2012 | Schechter et al. |
| 8,100,133 B2 | 1/2012 | Mintz et al. |
| 8,108,072 B2 | 1/2012 | Zhao et al. |
| 8,114,118 B2 | 2/2012 | Knodel et al. |
| 8,120,301 B2 | 2/2012 | Goldberg et al. |
| 8,127,975 B2 | 3/2012 | Olson et al. |
| 8,132,705 B2 | 3/2012 | Viola et al. |
| 8,142,447 B2 | 3/2012 | Cooper et al. |
| 8,147,503 B2 | 4/2012 | Zhao et al. |
| 8,151,661 B2 | 4/2012 | Schena et al. |
| 8,152,516 B2 | 4/2012 | Harvey et al. |
| 8,155,479 B2 | 4/2012 | Hoffman et al. |
| 8,157,150 B2 | 4/2012 | Viola et al. |
| 8,157,151 B2 | 4/2012 | Ingmanson et al. |
| 8,182,469 B2 | 5/2012 | Anderson et al. |
| 8,182,494 B1 | 5/2012 | Yencho et al. |
| 8,186,555 B2 | 5/2012 | Shelton, IV et al. |
| 8,186,587 B2 | 5/2012 | Zmood et al. |
| 8,202,278 B2 | 6/2012 | Orban, III et al. |
| 8,206,406 B2 | 6/2012 | Orban, III |
| 8,210,413 B2 | 7/2012 | Whitman et al. |
| 8,216,250 B2 | 7/2012 | Orban, III et al. |
| 8,220,367 B2 | 7/2012 | Hsu |
| 8,220,468 B2 | 7/2012 | Cooper et al. |
| 8,235,273 B2 | 8/2012 | Olson et al. |
| 8,237,388 B2 | 8/2012 | Jinno et al. |
| 8,241,322 B2 | 8/2012 | Whitman et al. |
| 8,256,319 B2 | 9/2012 | Cooper et al. |
| 8,272,554 B2 | 9/2012 | Whitman et al. |
| 8,285,517 B2 | 10/2012 | Sillman et al. |
| 8,292,150 B2 | 10/2012 | Bryant |
| 8,292,888 B2 | 10/2012 | Whitman |
| 8,315,720 B2 | 11/2012 | Mohr et al. |
| 8,335,590 B2 | 12/2012 | Costa et al. |
| 8,342,379 B2 | 1/2013 | Whitman et al. |
| 8,347,757 B2 | 1/2013 | Duval |
| 8,348,130 B2 | 1/2013 | Shah et al. |
| 8,348,855 B2 | 1/2013 | Hillely et al. |
| 8,353,440 B2 | 1/2013 | Whitman et al. |
| 8,357,144 B2 | 1/2013 | Whitman et al. |
| 8,365,633 B2 | 2/2013 | Simaan et al. |
| 8,365,972 B2 | 2/2013 | Aranyi et al. |
| 8,371,492 B2 | 2/2013 | Aranyi et al. |
| 8,372,057 B2 | 2/2013 | Cude et al. |
| 8,374,723 B2 | 2/2013 | Zhao et al. |
| 8,391,957 B2 | 3/2013 | Carlson et al. |
| 8,403,926 B2 | 3/2013 | Nobis et al. |
| 8,418,073 B2 | 4/2013 | Mohr et al. |
| 8,418,904 B2 | 4/2013 | Wenchell et al. |
| 8,419,717 B2 | 4/2013 | Diolaiti et al. |
| 8,423,182 B2 | 4/2013 | Robinson et al. |
| 8,424,739 B2 | 4/2013 | Racenet et al. |
| 8,452,447 B2 | 5/2013 | Nixon |
| 8,454,585 B2 | 6/2013 | Whitman |
| 8,465,476 B2 | 6/2013 | Rogers et al. |
| 8,499,992 B2 | 8/2013 | Whitman et al. |
| 8,505,802 B2 | 8/2013 | Viola et al. |
| 8,508,173 B2 | 8/2013 | Goldberg et al. |
| 8,517,241 B2 | 8/2013 | Nicholas et al. |
| 8,523,043 B2 | 9/2013 | Ullrich et al. |
| 8,528,440 B2 | 9/2013 | Morley et al. |
| 8,529,582 B2 | 9/2013 | Devengenzo et al. |
| 8,540,748 B2 | 9/2013 | Murphy et al. |
| 8,551,076 B2 | 10/2013 | Duval et al. |
| 8,551,116 B2 | 10/2013 | Julian et al. |
| 8,561,871 B2 | 10/2013 | Rajappa et al. |
| 8,561,874 B2 | 10/2013 | Scirica |
| 8,562,594 B2 | 10/2013 | Cooper et al. |
| 8,594,841 B2 | 11/2013 | Zhao et al. |
| 8,597,182 B2 | 12/2013 | Stein et al. |
| 8,597,280 B2 | 12/2013 | Cooper et al. |
| 8,600,551 B2 | 12/2013 | Itkowitz et al. |
| 8,602,287 B2 | 12/2013 | Yates et al. |
| 8,608,773 B2 | 12/2013 | Tierney et al. |
| 8,620,473 B2 | 12/2013 | Diolaiti et al. |
| 8,623,000 B2 | 1/2014 | Humayun et al. |
| 8,624,537 B2 | 1/2014 | Nowlin et al. |
| 8,627,995 B2 | 1/2014 | Smith et al. |
| 8,632,463 B2 | 1/2014 | Drinan et al. |
| 8,634,957 B2 | 1/2014 | Toth et al. |
| 8,636,192 B2 | 1/2014 | Farascioni et al. |
| 8,636,766 B2 | 1/2014 | Milliman et al. |
| 8,638,056 B2 | 1/2014 | Goldberg et al. |
| 8,638,057 B2 | 1/2014 | Goldberg et al. |
| 8,644,988 B2 | 2/2014 | Prisco et al. |
| 8,647,258 B2 | 2/2014 | Aranyi et al. |
| 8,652,121 B2 | 2/2014 | Quick et al. |
| 8,657,174 B2 | 2/2014 | Yates et al. |
| 8,657,177 B2 | 2/2014 | Scirica et al. |
| 8,666,544 B2 | 3/2014 | Moll et al. |
| 8,668,638 B2 | 3/2014 | Donhowe et al. |
| 8,672,206 B2 | 3/2014 | Aranyi et al. |
| 8,696,552 B2 | 4/2014 | Whitman |
| 8,708,213 B2 | 4/2014 | Shelton, IV et al. |
| 8,715,306 B2 | 5/2014 | Faller et al. |
| 8,746,252 B2 | 6/2014 | McGrogan et al. |
| 8,749,189 B2 | 6/2014 | Nowlin et al. |
| 8,749,190 B2 | 6/2014 | Nowlin et al. |
| 8,758,352 B2 | 6/2014 | Cooper et al. |
| 8,758,391 B2 | 6/2014 | Swayze et al. |
| 8,761,930 B2 | 6/2014 | Nixon |
| 8,768,516 B2 | 7/2014 | Diolaiti et al. |
| 8,784,410 B2 | 7/2014 | Dunning |
| 8,786,241 B2 | 7/2014 | Nowlin et al. |
| 8,790,243 B2 | 7/2014 | Cooper et al. |
| 8,806,973 B2 | 8/2014 | Ross et al. |
| 8,808,164 B2 | 8/2014 | Hoffman et al. |
| 8,808,311 B2 | 8/2014 | Heinrich et al. |
| 8,816,628 B2 | 8/2014 | Nowlin et al. |
| 8,820,605 B2 | 9/2014 | Shelton, IV |
| 8,821,480 B2 | 9/2014 | Burbank |
| 8,823,308 B2 | 9/2014 | Nowlin et al. |
| 8,827,989 B2 | 9/2014 | Niemeyer |
| 8,838,270 B2 | 9/2014 | Druke et al. |
| 8,851,355 B2 | 10/2014 | Aranyi et al. |
| 8,852,174 B2 | 10/2014 | Burbank |
| 8,858,547 B2 | 10/2014 | Brogna |
| 8,858,571 B2 | 10/2014 | Shelton, IV et al. |
| 8,862,268 B2 | 10/2014 | Robinson et al. |
| 8,864,751 B2 | 10/2014 | Prisco et al. |
| 8,864,752 B2 | 10/2014 | Diolaiti et al. |
| 8,875,972 B2 | 11/2014 | Weisenburgh, II et al. |
| 8,888,762 B2 | 11/2014 | Whitman |
| 8,893,946 B2 | 11/2014 | Boudreaux et al. |
| 8,899,462 B2 | 12/2014 | Kostrzewski et al. |
| 8,903,546 B2 | 12/2014 | Diolaiti et al. |
| 8,903,549 B2 | 12/2014 | Itkowitz et al. |
| 8,905,289 B2 | 12/2014 | Patel et al. |
| 8,911,428 B2 | 12/2014 | Cooper et al. |
| 8,912,746 B2 | 12/2014 | Reid et al. |
| 8,919,630 B2 | 12/2014 | Milliman |
| 8,925,786 B2 | 1/2015 | Holsten et al. |
| 8,931,680 B2 | 1/2015 | Milliman |
| 8,939,344 B2 | 1/2015 | Olson et al. |
| 8,944,070 B2 | 2/2015 | Guthart et al. |
| 8,950,646 B2 | 2/2015 | Viola |
| 8,960,519 B2 | 2/2015 | Whitman et al. |
| 8,961,396 B2 | 2/2015 | Azarbarzin et al. |

(56) References Cited

U.S. PATENT DOCUMENTS

| | | |
|---|---|---|
| 8,967,443 B2 | 3/2015 | McCuen |
| 8,968,276 B2 | 3/2015 | Zemlok et al. |
| 8,968,337 B2 | 3/2015 | Whitfield et al. |
| 8,989,903 B2 | 3/2015 | Weir et al. |
| 8,992,422 B2 | 3/2015 | Spivey et al. |
| 9,002,518 B2 | 4/2015 | Manzo et al. |
| 9,014,856 B2 | 4/2015 | Manzo et al. |
| 9,016,540 B2 | 4/2015 | Whitman et al. |
| 9,016,545 B2 | 4/2015 | Aranyi et al. |
| 9,019,345 B2 | 4/2015 | Patrick |
| 9,023,014 B2 | 5/2015 | Chowaniec et al. |
| 9,033,868 B2 | 5/2015 | Whitman et al. |
| 9,043,027 B2 | 5/2015 | Durant et al. |
| 9,050,120 B2 | 6/2015 | Swarup et al. |
| 9,055,943 B2 | 6/2015 | Zemlok et al. |
| 9,055,961 B2 | 6/2015 | Manzo et al. |
| 9,064,653 B2 | 6/2015 | Prest et al. |
| 9,068,628 B2 | 6/2015 | Solomon et al. |
| 9,072,515 B2 | 7/2015 | Hall et al. |
| 9,078,684 B2 | 7/2015 | Williams |
| 9,084,623 B2 | 7/2015 | Gomez et al. |
| 9,095,362 B2 | 8/2015 | Dachs, II et al. |
| 9,096,033 B2 | 8/2015 | Holop et al. |
| 9,101,381 B2 | 8/2015 | Burbank et al. |
| 9,113,847 B2 | 8/2015 | Whitman et al. |
| 9,113,875 B2 | 8/2015 | Viola et al. |
| 9,113,876 B2 | 8/2015 | Zemlok et al. |
| 9,113,877 B1 | 8/2015 | Whitman et al. |
| 9,113,899 B2 | 8/2015 | Garrison et al. |
| 9,138,284 B2 | 9/2015 | Krom et al. |
| 9,144,456 B2 | 9/2015 | Rosa et al. |
| 9,198,730 B2 | 12/2015 | Prisco et al. |
| 9,204,923 B2 | 12/2015 | Manzo et al. |
| 9,216,013 B2 | 12/2015 | Scirica et al. |
| 9,226,648 B2 | 1/2016 | Saadat et al. |
| 9,226,750 B2 | 1/2016 | Weir et al. |
| 9,226,761 B2 | 1/2016 | Burbank |
| 9,232,984 B2 | 1/2016 | Guthart et al. |
| 9,241,712 B2 | 1/2016 | Zemlok et al. |
| 9,241,766 B2 | 1/2016 | Duque et al. |
| 9,241,767 B2 | 1/2016 | Prisco et al. |
| 9,241,769 B2 | 1/2016 | Larkin et al. |
| 9,259,275 B2 | 2/2016 | Burbank |
| 9,259,277 B2 | 2/2016 | Rogers et al. |
| 9,259,281 B2 | 2/2016 | Griffiths et al. |
| 9,259,282 B2 | 2/2016 | Azizian et al. |
| 9,261,172 B2 | 2/2016 | Solomon et al. |
| 9,265,567 B2 | 2/2016 | Orban, III et al. |
| 9,265,584 B2 | 2/2016 | Itkowitz et al. |
| 9,282,961 B2 | 3/2016 | Whitman et al. |
| 9,282,963 B2 | 3/2016 | Bryant |
| 9,283,049 B2 | 3/2016 | Diolaiti et al. |
| 9,295,522 B2 | 3/2016 | Kostrzewski |
| 9,301,811 B2 | 4/2016 | Goldberg et al. |
| 9,307,986 B2 | 4/2016 | Hall et al. |
| 9,314,307 B2 | 4/2016 | Richmond et al. |
| 9,317,651 B2 | 4/2016 | Nixon |
| 9,345,546 B2 | 5/2016 | Toth et al. |
| 9,393,017 B2 | 7/2016 | Flanagan et al. |
| 9,402,689 B2 | 8/2016 | Prisco et al. |
| 9,417,621 B2 | 8/2016 | Diolaiti et al. |
| 9,424,303 B2 | 8/2016 | Hoffman et al. |
| 9,433,418 B2 | 9/2016 | Whitman et al. |
| 9,446,517 B2 | 9/2016 | Burns et al. |
| 9,452,020 B2 | 9/2016 | Griffiths et al. |
| 9,474,569 B2 | 10/2016 | Manzo et al. |
| 9,480,533 B2 | 11/2016 | Devengenzo et al. |
| 9,503,713 B2 | 11/2016 | Zhao et al. |
| 9,550,300 B2 | 1/2017 | Danitz et al. |
| 9,554,859 B2 | 1/2017 | Nowlin et al. |
| 9,566,124 B2 | 2/2017 | Prisco et al. |
| 9,579,164 B2 | 2/2017 | Itkowitz et al. |
| 9,585,641 B2 | 3/2017 | Cooper et al. |
| 9,615,883 B2 | 4/2017 | Schena et al. |
| 9,623,563 B2 | 4/2017 | Nixon |
| 9,623,902 B2 | 4/2017 | Griffiths et al. |
| 9,629,520 B2 | 4/2017 | Diolaiti |
| 9,662,177 B2 | 5/2017 | Weir et al. |
| 9,664,262 B2 | 5/2017 | Donlon et al. |
| 9,687,312 B2 | 6/2017 | Dachs, II et al. |
| 9,700,334 B2 | 7/2017 | Hinman et al. |
| 9,718,190 B2 | 8/2017 | Larkin et al. |
| 9,730,719 B2 | 8/2017 | Brisson et al. |
| 9,737,199 B2 | 8/2017 | Pistor et al. |
| 9,795,446 B2 | 10/2017 | DiMaio et al. |
| 9,797,484 B2 | 10/2017 | Solomon et al. |
| 9,801,690 B2 | 10/2017 | Larkin et al. |
| 9,814,530 B2 | 11/2017 | Weir et al. |
| 9,814,536 B2 | 11/2017 | Goldberg et al. |
| 9,814,537 B2 | 11/2017 | Itkowitz et al. |
| 9,820,823 B2 | 11/2017 | Richmond et al. |
| 9,827,059 B2 | 11/2017 | Robinson et al. |
| 9,830,371 B2 | 11/2017 | Hoffman et al. |
| 9,839,481 B2 | 12/2017 | Blumenkranz et al. |
| 9,839,487 B2 | 12/2017 | Dachs, II |
| 9,850,994 B2 | 12/2017 | Schena |
| 9,855,102 B2 | 1/2018 | Blumenkranz |
| 9,855,107 B2 | 1/2018 | Labonville et al. |
| 9,872,737 B2 | 1/2018 | Nixon |
| 9,877,718 B2 | 1/2018 | Weir et al. |
| 9,883,920 B2 | 2/2018 | Blumenkranz |
| 9,888,974 B2 | 2/2018 | Niemeyer |
| 9,895,813 B2 | 2/2018 | Blumenkranz et al. |
| 9,901,408 B2 | 2/2018 | Larkin |
| 9,918,800 B2 | 3/2018 | Itkowitz et al. |
| 9,937,626 B2 | 4/2018 | Rockrohr |
| 9,943,375 B2 | 4/2018 | Blumenkranz et al. |
| 9,948,852 B2 | 4/2018 | Lilagan et al. |
| 9,949,798 B2 | 4/2018 | Weir |
| 9,949,802 B2 | 4/2018 | Cooper |
| 9,952,107 B2 | 4/2018 | Blumenkranz et al. |
| 9,956,044 B2 | 5/2018 | Gomez et al. |
| 9,980,778 B2 | 5/2018 | Ohline et al. |
| 10,008,017 B2 | 6/2018 | Itkowitz et al. |
| 10,028,793 B2 | 7/2018 | Griffiths et al. |
| 10,033,308 B2 | 7/2018 | Chaghajerdi et al. |
| 10,034,719 B2 | 7/2018 | Richmond et al. |
| 10,052,167 B2 | 8/2018 | Au et al. |
| 10,085,811 B2 | 10/2018 | Weir et al. |
| 10,092,344 B2 | 10/2018 | Mohr et al. |
| 10,123,844 B2 | 11/2018 | Nowlin et al. |
| 10,179,413 B2 | 1/2019 | Rockrohr |
| 10,188,471 B2 | 1/2019 | Brisson |
| 10,201,390 B2 | 2/2019 | Swarup et al. |
| 10,213,202 B2 | 2/2019 | Flanagan et al. |
| 10,258,416 B2 | 4/2019 | Mintz et al. |
| 10,278,782 B2 | 5/2019 | Jarc et al. |
| 10,278,783 B2 | 5/2019 | Itkowitz et al. |
| 10,282,881 B2 | 5/2019 | Itkowitz et al. |
| 10,335,242 B2 | 7/2019 | Devengenzo et al. |
| 10,405,934 B2 | 9/2019 | Prisco et al. |
| 10,433,922 B2 | 10/2019 | Itkowitz et al. |
| 10,464,219 B2 | 11/2019 | Robinson et al. |
| 10,485,621 B2 | 11/2019 | Morrissette et al. |
| 10,500,004 B2 | 12/2019 | Hanuschik et al. |
| 10,500,005 B2 | 12/2019 | Weir et al. |
| 10,500,007 B2 | 12/2019 | Richmond et al. |
| 10,507,066 B2 | 12/2019 | DiMaio et al. |
| 10,510,267 B2 | 12/2019 | Jarc et al. |
| 10,524,871 B2 | 1/2020 | Liao |
| 10,548,459 B2 | 2/2020 | Itkowitz et al. |
| 10,575,909 B2 | 3/2020 | Robinson et al. |
| 10,592,529 B2 | 3/2020 | Hoffman et al. |
| 10,595,946 B2 | 3/2020 | Nixon |
| 10,881,469 B2 | 1/2021 | Robinson |
| 10,881,473 B2 | 1/2021 | Itkowitz et al. |
| 10,898,188 B2 | 1/2021 | Burbank |
| 10,898,189 B2 | 1/2021 | Mcdonald, II |
| 10,905,506 B2 | 2/2021 | Itkowitz et al. |
| 10,912,544 B2 | 2/2021 | Brisson et al. |
| 10,912,619 B2 | 2/2021 | Jarc et al. |
| 10,918,387 B2 | 2/2021 | Duque et al. |
| 10,918,449 B2 | 2/2021 | Solomon et al. |
| 10,932,873 B2 | 3/2021 | Griffiths et al. |

(56) References Cited

U.S. PATENT DOCUMENTS

| | | |
|---|---|---|
| 10,932,877 B2 | 3/2021 | Devengenzo et al. |
| 2001/0031975 A1 | 10/2001 | Whitman et al. |
| 2002/0040217 A1 | 4/2002 | Jinno |
| 2002/0049454 A1 | 4/2002 | Whitman et al. |
| 2002/0165541 A1 | 11/2002 | Whitman |
| 2003/0038938 A1 | 2/2003 | Jung et al. |
| 2003/0165794 A1 | 9/2003 | Matoba |
| 2003/0234685 A1* | 12/2003 | Ranmuthu .......... H03F 3/45475 330/86 |
| 2004/0034369 A1 | 2/2004 | Sauer et al. |
| 2004/0111012 A1 | 6/2004 | Whitman |
| 2004/0133189 A1 | 7/2004 | Sakurai |
| 2004/0153124 A1 | 8/2004 | Whitman |
| 2004/0176751 A1 | 9/2004 | Weitzner et al. |
| 2004/0193146 A1 | 9/2004 | Lee et al. |
| 2005/0125027 A1 | 6/2005 | Knodel et al. |
| 2005/0131442 A1 | 6/2005 | Yachia et al. |
| 2006/0072304 A1* | 4/2006 | Lay .......... F21S 9/022 362/157 |
| 2006/0079884 A1 | 4/2006 | Manzo et al. |
| 2006/0121778 A1* | 6/2006 | Huang .......... H05K 3/222 439/507 |
| 2006/0142656 A1 | 6/2006 | Malackowski et al. |
| 2006/0142740 A1 | 6/2006 | Sherman et al. |
| 2006/0142744 A1 | 6/2006 | Boutoussov |
| 2006/0235436 A1 | 10/2006 | Anderson et al. |
| 2006/0259073 A1 | 11/2006 | Miyamoto et al. |
| 2006/0278680 A1 | 12/2006 | Viola et al. |
| 2006/0284730 A1 | 12/2006 | Schmid et al. |
| 2007/0023476 A1 | 2/2007 | Whitman et al. |
| 2007/0023477 A1 | 2/2007 | Whitman et al. |
| 2007/0029363 A1 | 2/2007 | Popov |
| 2007/0084897 A1 | 4/2007 | Shelton et al. |
| 2007/0102472 A1 | 5/2007 | Shelton |
| 2007/0152014 A1 | 7/2007 | Gillum et al. |
| 2007/0175947 A1 | 8/2007 | Ortiz et al. |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0270784 A1 | 11/2007 | Smith et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0039256 A1 | 2/2008 | Jinno et al. |
| 2008/0058801 A1 | 3/2008 | Taylor et al. |
| 2008/0109012 A1 | 5/2008 | Falco et al. |
| 2008/0110958 A1 | 5/2008 | McKenna et al. |
| 2008/0114350 A1* | 5/2008 | Park .......... A61B 18/1206 600/509 |
| 2008/0119870 A1 | 5/2008 | Williams |
| 2008/0147089 A1 | 6/2008 | Loh et al. |
| 2008/0167736 A1 | 7/2008 | Swayze et al. |
| 2008/0185419 A1 | 8/2008 | Smith et al. |
| 2008/0188841 A1 | 8/2008 | Tomasello et al. |
| 2008/0197167 A1 | 8/2008 | Viola et al. |
| 2008/0208195 A1 | 8/2008 | Shores et al. |
| 2008/0237296 A1 | 10/2008 | Boudreaux et al. |
| 2008/0245175 A1 | 10/2008 | Jinno et al. |
| 2008/0251561 A1 | 10/2008 | Eades et al. |
| 2008/0255413 A1 | 10/2008 | Zemlok et al. |
| 2008/0255607 A1 | 10/2008 | Zemlok |
| 2008/0262654 A1 | 10/2008 | Omori et al. |
| 2008/0308603 A1 | 12/2008 | Shelton et al. |
| 2009/0012533 A1 | 1/2009 | Barbagli et al. |
| 2009/0090763 A1 | 4/2009 | Zemlok et al. |
| 2009/0099876 A1 | 4/2009 | Whitman |
| 2009/0138006 A1 | 5/2009 | Bales et al. |
| 2009/0163929 A1* | 6/2009 | Yeung .......... B25J 9/047 606/130 |
| 2009/0171147 A1 | 7/2009 | Lee et al. |
| 2009/0182193 A1 | 7/2009 | Whitman et al. |
| 2009/0209946 A1 | 8/2009 | Swayze et al. |
| 2009/0209990 A1 | 8/2009 | Yates et al. |
| 2009/0254094 A1 | 10/2009 | Knapp et al. |
| 2009/0299141 A1 | 12/2009 | Downey et al. |
| 2010/0016852 A1 | 1/2010 | Manzo et al. |
| 2010/0016853 A1 | 1/2010 | Burbank |
| 2010/0023022 A1 | 1/2010 | Zeiner et al. |
| 2010/0069939 A1* | 3/2010 | Konishi .......... A61B 90/98 606/169 |
| 2010/0069942 A1 | 3/2010 | Shelton, IV |
| 2010/0161921 A1* | 6/2010 | Berry, Jr. .......... G06F 8/66 711/E12.103 |
| 2010/0170519 A1 | 7/2010 | Romo et al. |
| 2010/0193568 A1 | 8/2010 | Scheib et al. |
| 2010/0211053 A1 | 8/2010 | Ross et al. |
| 2010/0225073 A1 | 9/2010 | Porter et al. |
| 2010/0228249 A1* | 9/2010 | Mohr .......... A61B 1/000096 715/764 |
| 2010/0228264 A1 | 9/2010 | Robinson et al. |
| 2010/0292708 A1 | 11/2010 | Madhani et al. |
| 2010/0319713 A1 | 12/2010 | Byers et al. |
| 2011/0071508 A1 | 3/2011 | Duval et al. |
| 2011/0077673 A1 | 3/2011 | Grubac et al. |
| 2011/0121049 A1 | 5/2011 | Malinouskas et al. |
| 2011/0125138 A1 | 5/2011 | Malinouskas et al. |
| 2011/0139851 A1 | 6/2011 | McCuen |
| 2011/0155783 A1 | 6/2011 | Rajappa et al. |
| 2011/0155786 A1 | 6/2011 | Shelton, IV |
| 2011/0172648 A1 | 7/2011 | Jeong |
| 2011/0174009 A1 | 7/2011 | Izuka et al. |
| 2011/0174099 A1 | 7/2011 | Ross et al. |
| 2011/0184245 A1 | 7/2011 | Xia et al. |
| 2011/0204119 A1 | 8/2011 | McCuen |
| 2011/0218522 A1 | 9/2011 | Whitman |
| 2011/0252678 A1* | 10/2011 | Jones .......... G09F 13/18 362/183 |
| 2011/0276057 A1 | 11/2011 | Conlon et al. |
| 2011/0290854 A1 | 12/2011 | Timm et al. |
| 2011/0295242 A1 | 12/2011 | Spivey et al. |
| 2011/0295269 A1 | 12/2011 | Swensgard et al. |
| 2012/0000962 A1 | 1/2012 | Racenet et al. |
| 2012/0010616 A1 | 1/2012 | Huang et al. |
| 2012/0040308 A1* | 2/2012 | Holbeche .......... A61C 1/0015 433/89 |
| 2012/0071752 A1 | 3/2012 | Sewell et al. |
| 2012/0074199 A1 | 3/2012 | Olson et al. |
| 2012/0080475 A1 | 4/2012 | Smith et al. |
| 2012/0080485 A1 | 4/2012 | Woodard, Jr. et al. |
| 2012/0089131 A1 | 4/2012 | Zemlok et al. |
| 2012/0104071 A1 | 5/2012 | Bryant |
| 2012/0116368 A1 | 5/2012 | Viola |
| 2012/0116416 A1 | 5/2012 | Neff et al. |
| 2012/0143002 A1 | 6/2012 | Aranyi et al. |
| 2012/0168485 A1 | 7/2012 | Marczyk et al. |
| 2012/0172924 A1 | 7/2012 | Allen, IV |
| 2012/0199630 A1 | 8/2012 | Shelton, IV |
| 2012/0223121 A1 | 9/2012 | Viola et al. |
| 2012/0245428 A1 | 9/2012 | Smith et al. |
| 2012/0253329 A1 | 10/2012 | Zemlok et al. |
| 2012/0298719 A1 | 11/2012 | Shelton, IV et al. |
| 2012/0310220 A1 | 12/2012 | Malkowski et al. |
| 2012/0323226 A1 | 12/2012 | Chowaniec et al. |
| 2012/0330285 A1 | 12/2012 | Hartoumbekis et al. |
| 2013/0020376 A1 | 1/2013 | Shelton, IV et al. |
| 2013/0032629 A1 | 2/2013 | Viola |
| 2013/0093149 A1 | 4/2013 | Saur et al. |
| 2013/0110129 A1* | 5/2013 | Reid .......... A61B 34/30 403/326 |
| 2013/0131695 A1 | 5/2013 | Scarfogliero et al. |
| 2013/0158542 A1 | 6/2013 | Manzo et al. |
| 2013/0181035 A1 | 7/2013 | Milliman |
| 2013/0184704 A1 | 7/2013 | Beardsley et al. |
| 2013/0209208 A1* | 8/2013 | Bailey .......... B25J 9/1065 414/728 |
| 2013/0214025 A1 | 8/2013 | Zemlok et al. |
| 2013/0274722 A1 | 10/2013 | Kostrzewski et al. |
| 2013/0282052 A1 | 10/2013 | Aranyi et al. |
| 2013/0292451 A1 | 11/2013 | Viola et al. |
| 2013/0313304 A1 | 11/2013 | Shelton, IV et al. |
| 2013/0317486 A1 | 11/2013 | Nicholas et al. |

(56) References Cited

U.S. PATENT DOCUMENTS

| | | |
|---|---|---|
| 2013/0319706 A1 | 12/2013 | Nicholas et al. |
| 2013/0324978 A1 | 12/2013 | Nicholas et al. |
| 2013/0324979 A1 | 12/2013 | Nicholas et al. |
| 2013/0325095 A1 | 12/2013 | Ollivier |
| 2013/0334281 A1 | 12/2013 | Williams |
| 2014/0005640 A1 | 1/2014 | Shelton, IV et al. |
| 2014/0012236 A1 | 1/2014 | Williams et al. |
| 2014/0012237 A1 | 1/2014 | Pribanic et al. |
| 2014/0012289 A1 | 1/2014 | Snow et al. |
| 2014/0025046 A1 | 1/2014 | Williams et al. |
| 2014/0028288 A1* | 1/2014 | Peck ............... H02J 13/00016 324/126 |
| 2014/0110455 A1 | 4/2014 | Ingmanson et al. |
| 2014/0166023 A1 | 6/2014 | Kishi |
| 2014/0207125 A1 | 7/2014 | Applegate et al. |
| 2014/0207182 A1 | 7/2014 | Zergiebel et al. |
| 2014/0207185 A1 | 7/2014 | Goble et al. |
| 2014/0236174 A1 | 8/2014 | Williams et al. |
| 2014/0276932 A1 | 9/2014 | Williams et al. |
| 2014/0299647 A1 | 10/2014 | Scirica et al. |
| 2014/0303668 A1 | 10/2014 | Nicholas et al. |
| 2014/0358129 A1 | 12/2014 | Zergiebel et al. |
| 2014/0361068 A1 | 12/2014 | Aranyi et al. |
| 2014/0365235 A1 | 12/2014 | DeBoer et al. |
| 2014/0373652 A1 | 12/2014 | Zergiebel et al. |
| 2014/0378761 A1 | 12/2014 | Zorn et al. |
| 2015/0014392 A1 | 1/2015 | Williams et al. |
| 2015/0048144 A1 | 2/2015 | Whitman |
| 2015/0076205 A1 | 3/2015 | Zergiebel |
| 2015/0080912 A1 | 3/2015 | Sapre |
| 2015/0090063 A1 | 4/2015 | Lantermann et al. |
| 2015/0112381 A1 | 4/2015 | Richard |
| 2015/0122870 A1 | 5/2015 | Zemlok et al. |
| 2015/0133224 A1 | 5/2015 | Whitman et al. |
| 2015/0150547 A1 | 6/2015 | Ingmanson et al. |
| 2015/0150574 A1 | 6/2015 | Richard et al. |
| 2015/0157320 A1 | 6/2015 | Zergiebel et al. |
| 2015/0157321 A1 | 6/2015 | Zergiebel et al. |
| 2015/0164502 A1 | 6/2015 | Richard et al. |
| 2015/0201931 A1 | 7/2015 | Zergiebel et al. |
| 2015/0202009 A1 | 7/2015 | Nussbaumer et al. |
| 2015/0272577 A1 | 10/2015 | Zemlok et al. |
| 2015/0297199 A1 | 10/2015 | Nicholas et al. |
| 2015/0303996 A1 | 10/2015 | Calderoni |
| 2015/0320420 A1 | 11/2015 | Penna et al. |
| 2015/0327850 A1 | 11/2015 | Kostrzewski |
| 2015/0342601 A1 | 12/2015 | Williams et al. |
| 2015/0342603 A1 | 12/2015 | Zergiebel et al. |
| 2015/0374366 A1 | 12/2015 | Zergiebel et al. |
| 2015/0374370 A1 | 12/2015 | Zergiebel et al. |
| 2015/0374371 A1 | 12/2015 | Richard et al. |
| 2015/0374372 A1 | 12/2015 | Zergiebel et al. |
| 2015/0374449 A1 | 12/2015 | Chowaniec et al. |
| 2015/0380187 A1 | 12/2015 | Zergiebel et al. |
| 2016/0095585 A1 | 4/2016 | Zergiebel et al. |
| 2016/0095596 A1 | 4/2016 | Scirica et al. |
| 2016/0106406 A1 | 4/2016 | Cabrera et al. |
| 2016/0113648 A1 | 4/2016 | Zergiebel et al. |
| 2016/0113649 A1 | 4/2016 | Zergiebel et al. |
| 2016/0184036 A1* | 6/2016 | Solomon ............... B25J 9/1641 606/130 |
| 2016/0270842 A1* | 9/2016 | Strobl ............... A61B 18/1445 |
| 2018/0168748 A1 | 6/2018 | Kapadia |

FOREIGN PATENT DOCUMENTS

| | | |
|---|---|---|
| CN | 1957854 A | 5/2007 |
| CN | 101495046 A | 7/2009 |
| CN | 102247182 A | 11/2011 |
| CN | 103732174 A | 4/2014 |
| CN | 105611894 A | 5/2016 |
| DE | 102008053842 A1 | 5/2010 |
| EP | 0443576 A1 | 8/1991 |
| EP | 0705571 A1 | 4/1996 |
| EP | 1563793 A1 | 8/2005 |
| EP | 1769754 A1 | 4/2007 |
| EP | 2316345 A1 | 5/2011 |
| EP | 2668910 A2 | 12/2013 |
| EP | 3416582 A1 | 12/2018 |
| ES | 2333509 A1 | 2/2010 |
| JP | 2003325543 A | 11/2003 |
| JP | 2005125075 A | 5/2005 |
| JP | 2015535193 A | 12/2015 |
| KR | 20120022521 A | 3/2012 |
| WO | 2011016640 A2 | 2/2011 |
| WO | 2011108840 A2 | 9/2011 |
| WO | 2012/040984 A1 | 4/2012 |
| WO | 2015088647 A1 | 6/2015 |
| WO | 2016043845 A1 | 3/2016 |

OTHER PUBLICATIONS

Japanese Office Action dated Jun. 7, 2022 for application No. 2020-513822 with English translation.

Communication Pursuant to Article 94(3) EPC issued in corresponding European Application No. 18 853 986.0 dated Jul. 24, 2024, 6 pages.

* cited by examiner

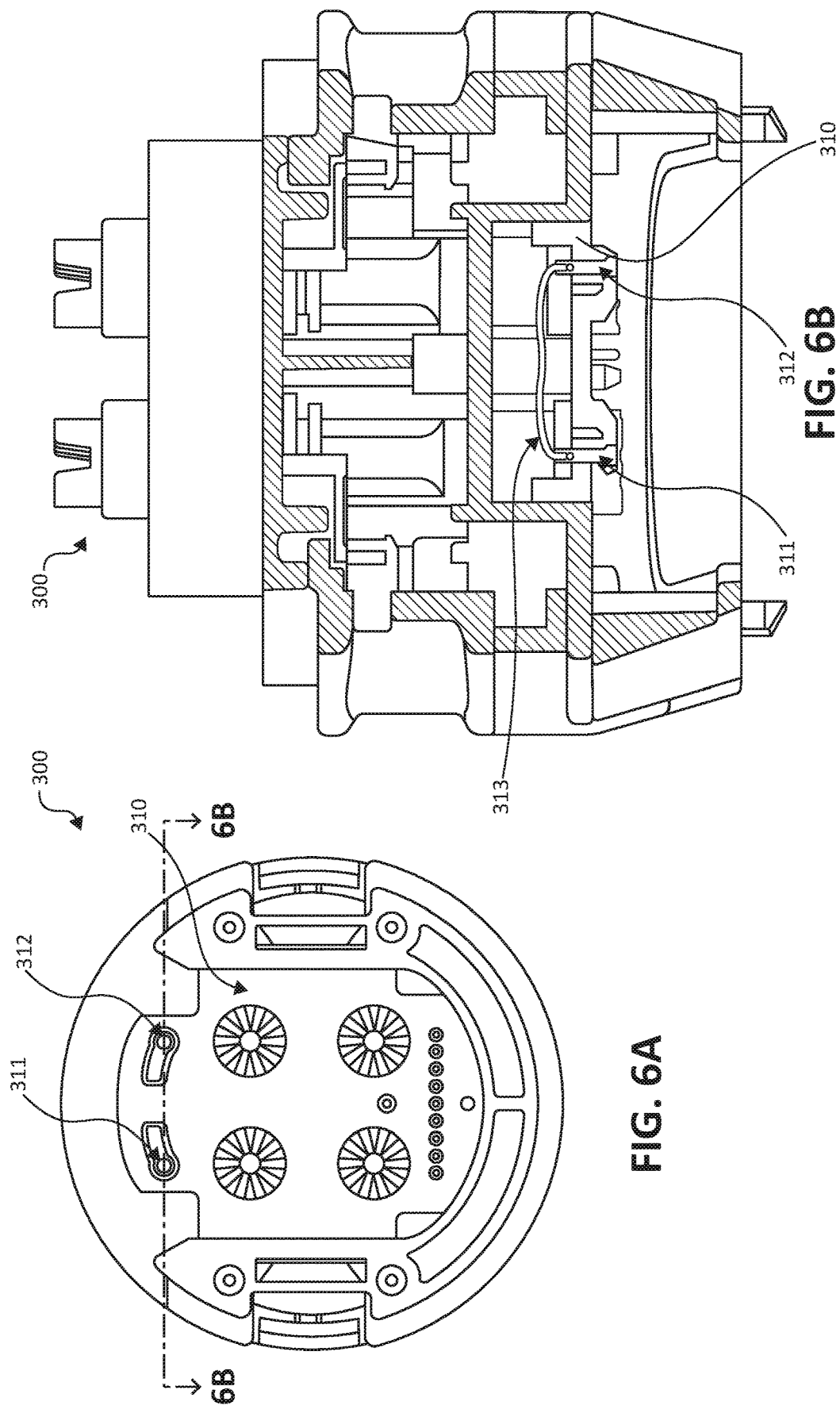

ENERGY DISCONNECT FOR ROBOTIC SURGICAL ASSEMBLIES

CROSS-REFERENCE TO RELATED APPLICATIONS

This application is a U.S. National Stage Application filed under 35 U.S.C. § 371 (a) of International Patent Application Serial No. PCT/US2018/049632, filed Sep. 6, 2018, which claims the benefit of and priority to U.S. Provisional Patent Application Ser. No. 62/555,936, filed Sep. 8, 2017, the entire disclosure of which is incorporated by reference herein.

TECHNICAL FIELD

The present disclosure relates to robotics, and more specifically to robotic surgical devices, assemblies, and/or systems for performing endoscopic surgical procedures and methods of use thereof.

BACKGROUND

Robotically-assisted surgery is increasingly being used in minimally invasive medical procedures. Some robotic surgical systems include a console supporting a surgical robotic arm and a robotic surgical instrument mounted to the robotic arm. The robotic surgical instrument may have an elongated shaft that supports at least one end effector (e.g., forceps or a grasping tool) on a distal end thereof.

Although robotically-assisted surgery may have certain advantages over other forms of surgery, robotic surgical systems may reduce tangible feedback that a clinician may otherwise have with a hand-operated surgical instrument. For example, with a hand-operated surgical instrument, a clinician can easily determine (e.g., by visual and/or tactile perception) when an electrosurgical cord is attached and/or powering the hand-operated instrument. With robotic surgical systems, a clinician is often positioned remote from the robotic surgical instrument and may not be able to readily ascertain such tangible feedback, requiring the clinician to be more cognizant of the robotic surgical instrument's electrical connection to an electrosurgical energy source.

In certain instances, this robotic surgical instrument may be removed from the robotic arm during an instrument exchange while still connected to an electrosurgical energy source. The robotic surgical instrument is then placed in the operating theater so that it may be reattached for subsequent reuse. Without having the tangible feedback advantage provided by hand-operated surgical instruments, the clinician is required to take the added step of unplugging the robotic surgical instrument from the electrosurgical energy source in order to avoid inadvertent activation while the robotic surgical instrument is separated from the robotic arm. Also, when reuse is required, besides reconnecting the robotic surgical instrument back to the robotic arm, the clinician is also required to take the additional step of reattaching the robotic surgical instrument to the electrosurgical energy source.

Thus, a need exists for a system that enables a robotic surgical instrument to be efficiently coupled and uncoupled to a robotic arm, and which mitigates the risk of inadvertently activating electrosurgical energy on a robotic surgical instrument.

SUMMARY

Accordingly, one aspect of the present disclosure is directed to a robotic surgical system. The robotic surgical system includes an electrosurgical energy source, an instrument drive unit, a sterile interface module coupled to the instrument drive unit, and a robotic surgical instrument selectively couplable to the sterile interface module. The robotic surgical instrument may be disposed in electrical communication with the electrosurgical energy source while the robotic surgical instrument is coupled to the sterile interface module. The robotic surgical instrument is configured to automatically electrically disconnect from the electrosurgical energy source when the robotic surgical instrument is uncoupled from the sterile interface module.

In some embodiments, the robotic surgical instrument may include a first electrical connector coupled to the electrosurgical energy source and configured to electrically couple to the sterile interface module.

In certain embodiments, the robotic surgical instrument may include a second electrical connector in electrical communication with an end effector of the robotic surgical instrument. The first and second electrical connectors of the robotic surgical instrument may be electrically isolated from each other when the robotic surgical instrument is uncoupled from the sterile interface module.

In embodiments, an electrical wiring may couple the second electrical connector of the robotic surgical instrument to the end effector.

In some embodiments, the sterile interface module may include first and second electrical connectors configured for electrical communication with the first and second electrical connectors of the robotic surgical instrument.

In certain embodiments, an electrical wiring may couple the first and second electrical connectors of the sterile interface module.

In embodiments, when the robotic surgical instrument is coupled to the sterile interface module, the first and second electrical connectors of the robotic surgical instrument may be in electrical communication with the first and second electrical connectors of the sterile interface module such that the robotic surgical instrument and the sterile interface module form a closed circuit.

In some embodiments, when the robotic surgical instrument is uncoupled from the sterile interface module, the first and second electrical connectors of the robotic surgical instrument may be electrically isolated from the first and second electrical connectors of the sterile interface module.

In certain embodiments, the robotic surgical instrument may include a third electrical connector in electrical communication with the electrosurgical energy source and the first electrical connector of the robotic surgical instrument.

In embodiments, the first electrical connector of the robotic surgical instrument may be a pogo pin.

According to another aspect, the present disclosure is directed to a robotic surgical system, including an electrosurgical energy source, an instrument drive unit, a sterile interface module coupled to the instrument drive unit and including a first electrical connector. The robotic surgical instrument may include a first electrical connector and may be selectively couplable to the sterile interface module. The first electrical connector of the robotic surgical instrument may be configured to couple to the first electrical connector of the sterile interface module when the robotic surgical instrument is coupled to the sterile interface module.

The robotic surgical instrument may be disposed in electrical communication with the electrosurgical energy source while the first electrical connector of the robotic surgical instrument is coupled to the first electrical connector of the sterile interface module. The robotic surgical instrument may be configured to electrically disconnect from the electrosurgical energy source when the robotic surgical instrument is uncoupled from the sterile interface module.

In embodiments, the first electrical connector of the robotic surgical instrument may be coupled to the electrosurgical energy source. The robotic surgical instrument may include a second electrical connector in electrical communication with an end effector of the robotic surgical instrument. The first and second electrical connectors of the robotic surgical instrument electrically may be isolated from each other when the robotic surgical instrument is uncoupled from the sterile interface module.

In some embodiments, an electrical wiring may couple the second electrical connector of the robotic surgical instrument to the end effector.

In certain embodiments, the sterile interface module may include a second electrical connector coupled to the first electrical connector of the sterile interface module.

In embodiments, an electrical wiring may couple the first and second electrical connectors of the sterile interface module.

In some embodiments, a floating plate may be disposed within the sterile interface module. The floating plate may support the first and second electrical connectors and the electrical wiring and may be configured to move from a first position to a second position within the sterile interface module. When the floating plate moves from the first position to the second position, the first and second electrical connectors of the sterile interface module may electrically disconnect from the first and second electrical connectors of the robotic surgical instrument.

In certain embodiments, when the robotic surgical instrument is coupled to the sterile interface module, the first and second electrical connectors of the robotic surgical instrument may be in electrical communication with the first and second electrical connectors of the sterile interface module such that the robotic surgical instrument and the sterile interface module form a closed circuit.

In embodiments, the first and second electrical connectors of the robotic surgical instrument and the sterile interface module may be pogo pins.

According to another aspect of the present disclosure, a method for selectively electrically activating a robotic surgical instrument is provided. The method may include coupling the robotic surgical instrument to an electrosurgical energy source and loading the robotic surgical instrument onto a sterile interface module while the robotic surgical instrument is coupled to the electrosurgical energy source. The method may include electrically coupling a jumper assembly of the sterile interface module to at least one electrical component of the robotic surgical instrument to enable electrosurgical energy to be conducted through the robotic surgical instrument and the sterile interface module upon loading the robotic surgical instrument onto the sterile interface module.

In embodiments, the method may include selectively unloading the robotic surgical instrument from the sterile interface module to automatically electrically deactivate the robotic surgical instrument while the robotic surgical instrument is coupled to the electrosurgical energy source.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description given below, serve to explain the principles of the disclosure, wherein:

FIG. 6A is a bottom view of another embodiment of a sterile interface module; and FIG. 6B is a side, partial cross-sectional view of the sterile interface module of FIG. 6A as taken along section line 6B-6B shown in FIG. 6A.

DETAILED DESCRIPTION

Figure 1:
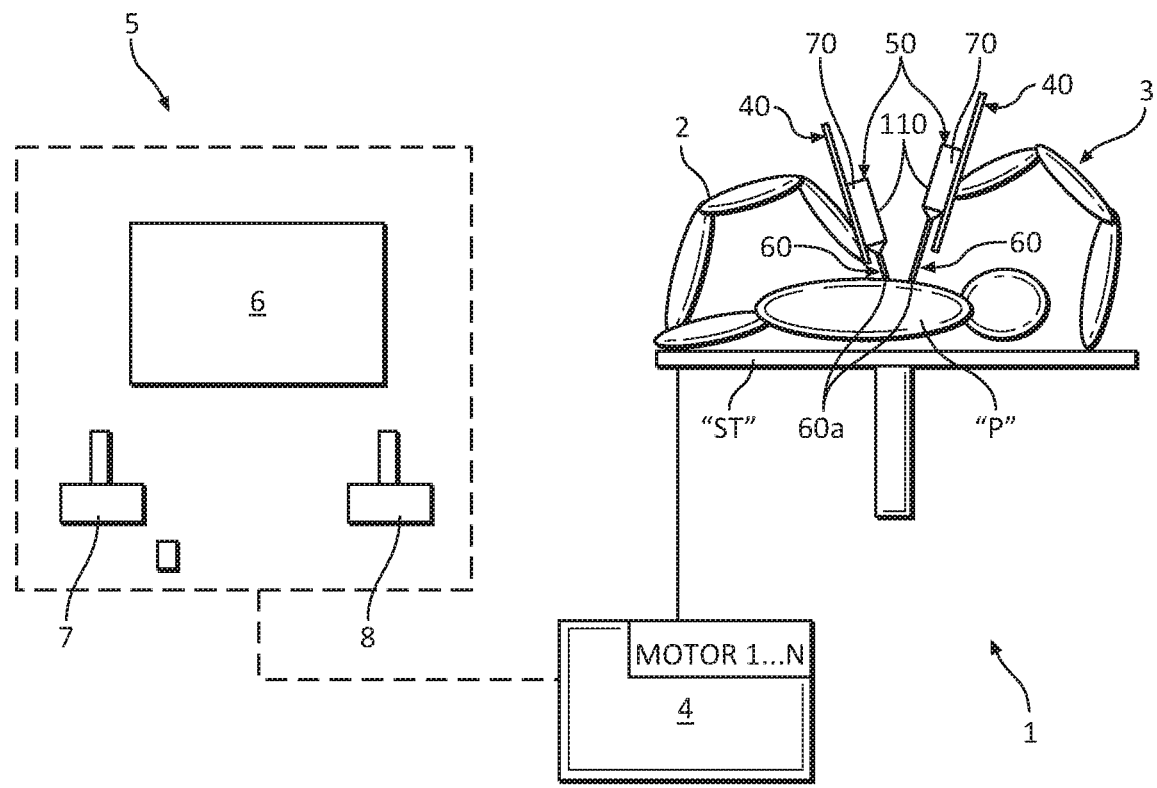
FIG. 1 is a schematic illustration of a robotic surgical system in accordance with the present disclosure.

Embodiments of the present disclosure are described in detail with reference to the drawings, in which like reference numerals designate identical or corresponding elements in each of the several views. As used herein, the term "distal" refers to that portion of structure that is closer to a patient, while the term "proximal" refers to that portion of structure that is farther from the patient. As used herein, the term "clinician" refers to a doctor, nurse, or other care provider and may include support personnel. In the following description, well-known functions or construction are not described in detail to avoid obscuring the present disclosure in unnecessary detail.

Figure 2B:
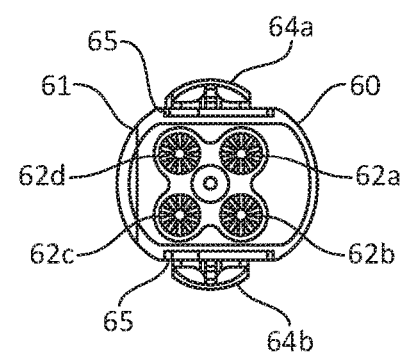
FIG. 2B is a top view of one embodiment of an electromechanical surgical instrument of the robotic surgical assembly shown in FIG. 2A.
Figure 2A:
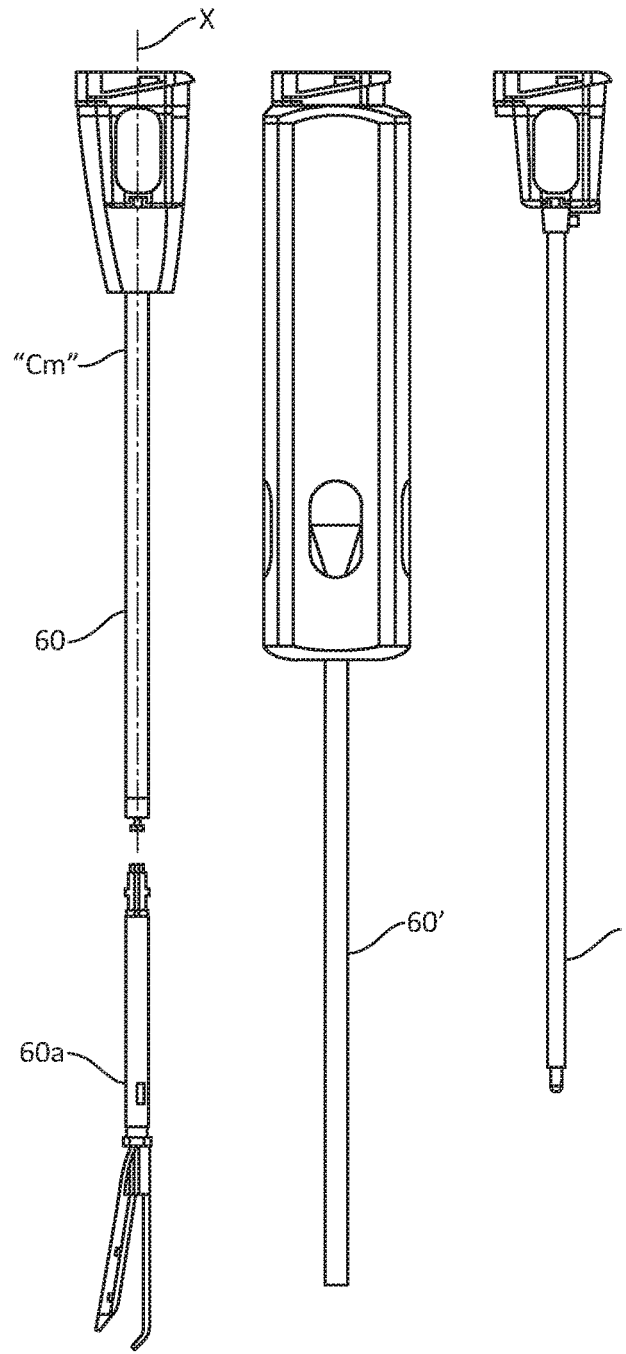
FIG. 2A is a side, elevational view, with parts separated, illustrating an embodiment of a robotic surgical assembly of the robotic surgical system of FIG. 1.
Figure 2A:
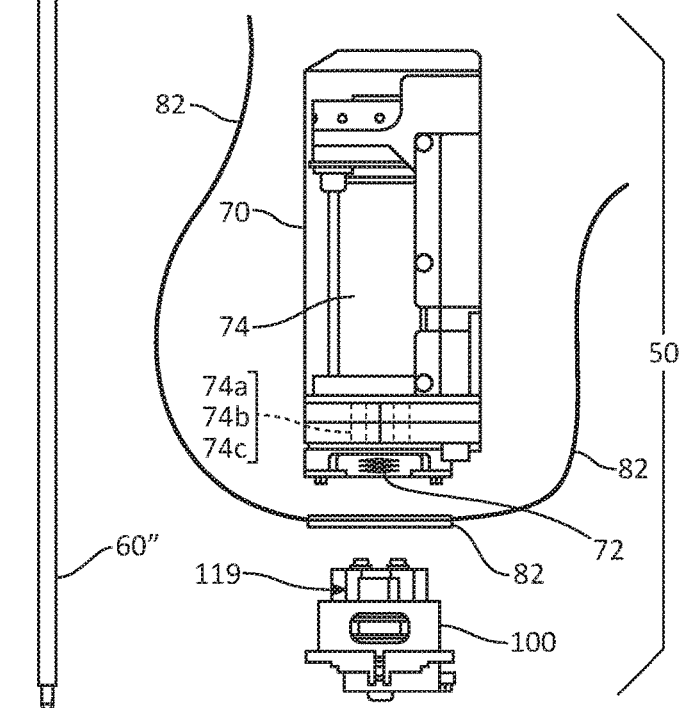
Figure 4:
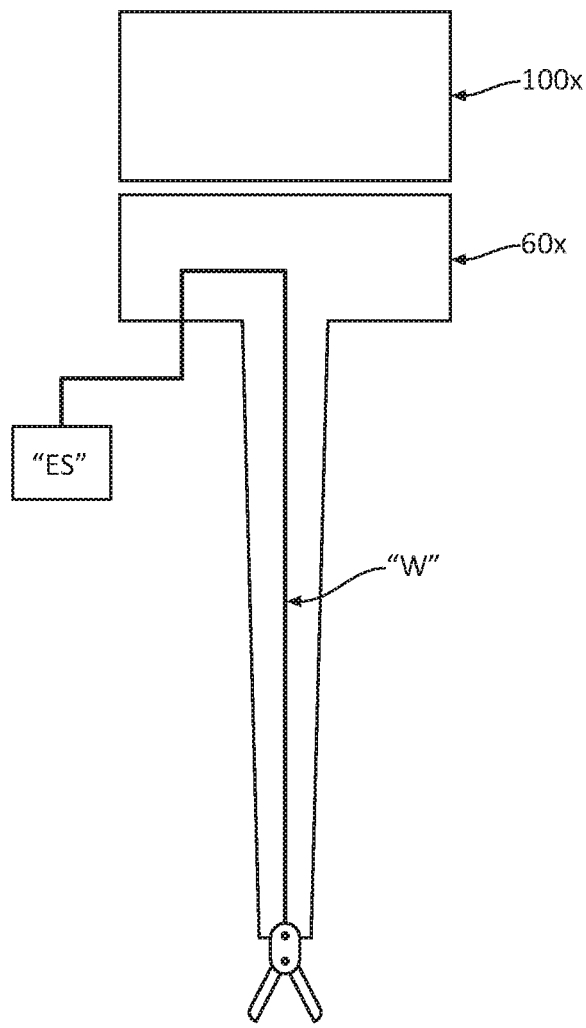
FIG. 4 is a side, elevational view illustrating a sterile interface module coupled to an electromechanical surgical instrument.

Referring initially to FIGS. 1 and 2A, a surgical system, such as, for example, a robotic surgical system 1, generally includes one or more surgical robotic arms 2, 3, a control device 4, and an operating console 5 coupled with control device 4. Any of surgical robotic arms 2, 3 may have a robotic surgical assembly 50 and an electromechanical surgical instrument 60 coupled thereto. Robotic surgical assembly 50 further includes an instrument drive unit 70 and a collar assembly or sterile interface module, such as sterile interface module 100 or sterile interface module 100*x* (FIG. 4), that couple to an electromechanical surgical instrument, such as electromechanical surgical instrument 60 or electromechanical surgical instrument 60*x* (FIG. 4), to instrument drive unit 70.

Surgical system 1 may also include an electrosurgical energy source "ES," such as a generator, to which the robotic surgical assembly 50, electromechanical surgical instruments 60 (FIG. 2A) or 60*x* (FIG. 4), instrument drive unit 70, and/or sterile interface modules 100 (FIG. 2A) or 100*x* (FIG. 4) may be electrically coupled. Although energy source "ES" may include any suitable energy source, for a more detailed description of one example of an electrosurgical generator, reference can be made to U.S. Pat. No. 8,784,410, the entire contents of which are incorporated by reference herein.

In general, while electromechanical surgical instrument 60x (FIG. 4) may be configured to maintain electrical connection with electrosurgical energy source "ES" when sterile interface module 100x (FIG. 4) and electromechanical surgical instrument 60x are uncoupled, electromechanical surgical instrument 60 (FIG. 2A) may be configured to break electrical connection with electrosurgical energy source "ES" when sterile interface module 100 and electromechanical surgical instrument 60 are uncoupled. More specifically, sterile interface module 100 and electromechanical surgical instrument 60 can be configured to cooperate to provide an electrical disconnect system that electrically disconnects electromechanical surgical instrument 60 from electrosurgical energy source "ES" when sterile interface module 100 and electromechanical surgical instrument 60 are uncoupled (see FIGS. 5A and 5B).

In some embodiments, robotic surgical assembly 50 may be removably attached to a slide rail 40 of one of surgical robotic arms 2, 3. In certain embodiments, robotic surgical assembly 50 may be fixedly attached to slide rail 40 of one of surgical robotic arms 2, 3.

Operating console 5 includes a display device 6, which is configured to display three-dimensional images, and manual input devices 7, 8, by means of which a clinician (not shown), is able to telemanipulate robotic arms 2, 3 in a first operating mode, as known in principle to a person skilled in the art. Each of robotic arms 2, 3 may be composed of any number of members, which may be connected through joints. Robotic arms 2, 3 may be driven by electric drives (not shown) that are connected to control device 4. Control device 4 (e.g., a computer) is set up to activate the drives, for example, by means of a computer program, in such a way that robotic arms 2, 3, attached robotic surgical assembly 50, and thus any attached electromechanical surgical instrument (including an electromechanical end effector thereof configured for activation or firing of an electrosurgical energy-based instrument or the like) execute a desired movement according to a movement defined by means of manual input devices 7, 8. Control device 4 may also be set up in such a way that it regulates the movement of robotic arms 2, 3 and/or of the drives.

Robotic surgical system 1 is configured for use on a patient "P" positioned (e.g., lying) on a surgical table "ST" to be treated in a minimally invasive manner by means of a surgical instrument, e.g., any suitable electromechanical surgical instrument, such as straight/articulatable instruments 60 (e.g., stapling instrument, suturing instrument, electrocautery instrument, etc.), endoscope 60' or grasper 60" (FIG. 2A). Robotic surgical system 1 may also include more than two robotic arms 2, 3, the additional robotic arms likewise connected to control device 4 and telemanipulatable by means of operating console 5. A surgical instrument, for example, electromechanical surgical instrument 60, may also be attached to any additional robotic arm(s).

Control device 4 may control one or more motors, e.g., motors (Motor 1 . . . n), each motor configured to drive movement of robotic arms 2, 3 in any number of directions. Further, control device 4 may control instrument drive unit 70 including a motor assembly 74 thereof that drives various operations of an end effector, such as an end effector 60a of electromechanical surgical instrument 60.

With reference to FIG. 1, motor assembly 74 of robotic surgical assembly 50 includes any number of motors 74a, 74b, 74c, etc. that couple to sterile interface module 100 via a corresponding number of motor couplers 76, such as motor couplers 76a, 76b, 76c, etc. (FIG. 3) extending from motors 74a, 74b, 74c, etc.

In general, robotic surgical assembly 50 transfers power and actuation forces from motors 74a, 74b, 74c, etc. to motor couplers 76a, 76b, 76c, etc. of motor assembly 74, through sterile interface module 100, to driven members 62a, 62b, 62c, etc. (see FIG. 2B) supported within an instrument housing 61 of electromechanical surgical instrument 60. Such transfer of power and actuation forces ultimately drives movement of components of end effector 60a of electromechanical surgical instrument 60 for operating electromechanical surgical instrument 60. This movement may include, for example, a movement of a knife blade (not shown) and/or a closing and opening of jaw members of end effector 60a, an articulation/rotation/pitch/yaw of end effector 60a, and/or the actuation or firing of end effector 60a (e.g. a stapling portion of end effector 60a).

Reference may be made to commonly owned International Patent Application No. PCT/US14/61329, U.S. Pat. No. 8,636,192, or 8,925,786, the entire disclosures of each of which are incorporated by reference herein, for a detailed discussion of illustrative examples of the construction and operation of end effectors for use with, or connection to, the presently disclosed electromechanical surgical instruments.

For a detailed discussion of the construction and operation of a similar robotic surgical system having one or more of the same or similar components for use with one or more components of the presently described robotic surgical system, reference may be made to U.S. Patent Application Publication No. 2012/0116416, the entire disclosure of which is incorporated by reference herein.

With reference to FIG. 2A, instrument drive unit 70 supports sterile interface module 100 for coupling electromechanical surgical instrument 60 to instrument drive unit 70. A distal or leading end portion of instrument drive unit 70 includes one or more buttons 72 that are depressible to selectively attach and/or release sterile interface module 100 to/from instrument drive unit 70.

The distal end portion of instrument drive unit 70 further supports a ring member 80 having a sterile drape 82 secured thereto. Sterile drape 82 is configured to overlie robotic surgical assembly 50 and robotic arms 2, 3 and may be arranged as desired to provide a sterile barrier between the various aforementioned components and/or the surgical site/fluids and electromechanical surgical instrument 60.

Figure 3:
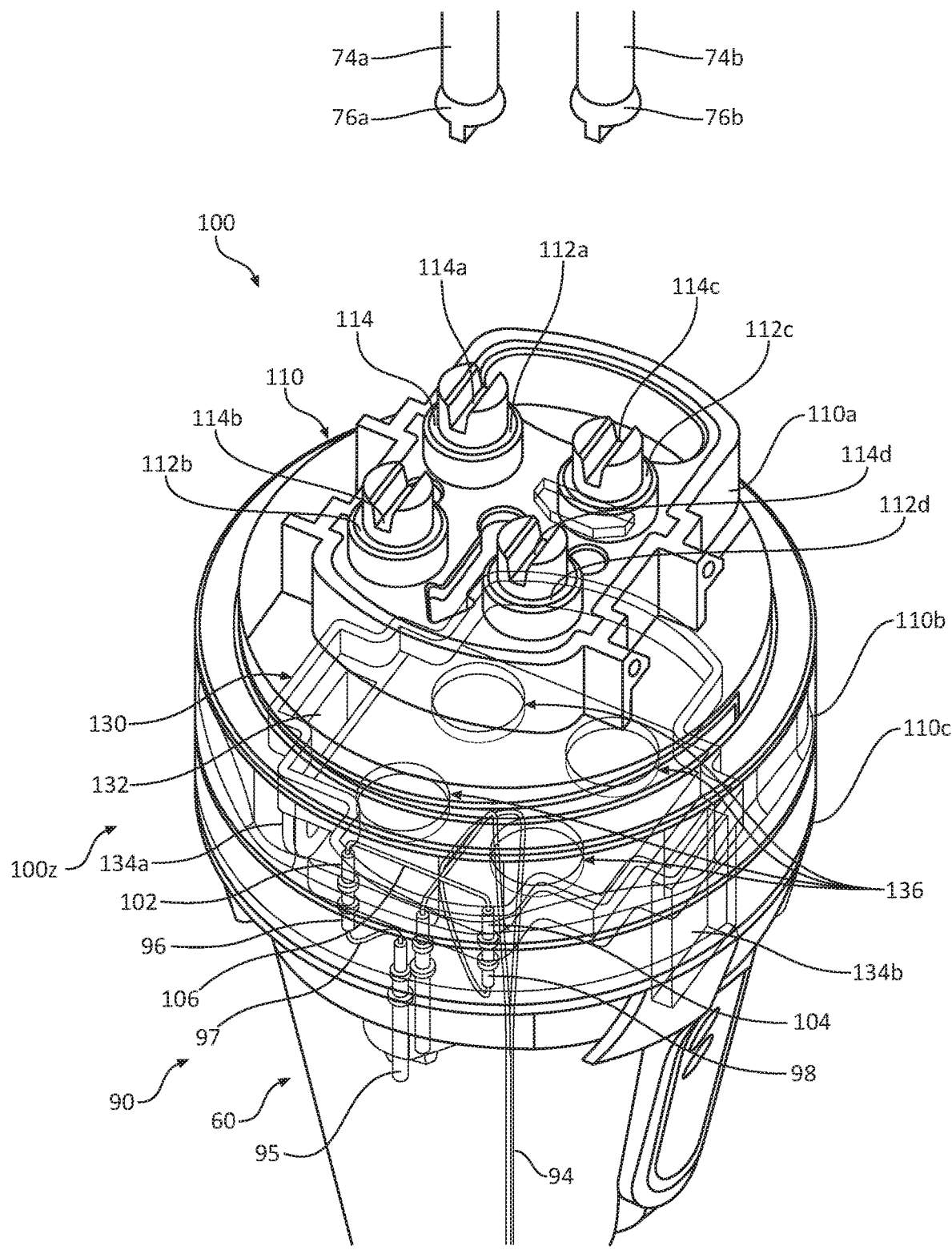
FIG. 3 is a perspective view illustrating a portion of the robotic surgical assembly of FIG. 2A with one embodiment of a sterile interface module of the robotic surgical assembly of FIG. 2A coupled to one embodiment of an electromechanical surgical instrument of the robotic surgical assembly of FIG. 2A.

With reference to FIGS. 2A and 3, sterile interface module 100 of robotic surgical assembly 50 is provided for selectively interconnecting or interfacing instrument drive unit 70 and an electromechanical surgical instrument such as electromechanical surgical instrument 60. Electromechanical surgical instrument 60 may be laterally coupled (e.g., side-loaded) to, or laterally decoupled from, sterile interface module 100. Advantageously, sterile interface module 100 maintains sterility, provides a means to transmit electrical communication between instrument drive unit 70 and electromechanical surgical instrument 60, provides structure configured to transfer rotational force from instrument drive unit 70 to electromechanical surgical instrument 60 for performing a function with electromechanical surgical instrument 60, and/or provides structure to selectively attach/remove electromechanical surgical instrument 60 to/from robotic surgical assembly 50 (e.g., for rapid instrument exchange).

As seen in FIG. 3, sterile interface module 100 of robotic surgical assembly 50 includes a body member 110 having an upper portion 110a, an intermediate portion 110b, and a lower portion 110c. Body member 110 defines drive transfer channels 112a, 112b, 112c, 112d therethrough that support drive transfer assemblies 114, such as respective drive transfer assemblies 114a, 114b, 114c, 114d, therein. Proximal end portions of drive transfer assemblies 114a, 114b, 114c, 114d of sterile interface module 100 are selectively engagable with respective motor couplers 76a, 76b, 76c, etc. of instrument drive unit 70, and distal end portions of drive transfer assemblies 114a, 114b, 114c, 114d are selectively engagable with respective driven member 62a, 62b, 62c, etc. of an electromechanical surgical instrument, such as electromechanical surgical instrument 60, to selectively operate an end effector 60a of electromechanical surgical instrument 60, for example.

Sterile interface module 100 further includes a floating plate 130 supported between intermediate portion 110b of the body member 110 and lower portion 110c of body member 110. Floating plate 130 includes a base portion 132 and tabs 134a, 134b that extend distally from base portion 132. Tabs 134a, 134b of floating plate 130 extend through lower portion 110c of body member 110. Floating plate 130 defines apertures 136 therein that receive drive transfer assemblies 114a, 114b, 114c, 114d of sterile interface module 100. Floating plate 130 is movable between an uncompressed or extended position and a compressed or retracted position to enable sterile interface module 100 to selectively couple to an electromechanical surgical instrument such as electromechanical surgical instrument 60. Floating plate 130 is spring biased distally toward the uncompressed position by drive transfer assemblies 114a, 114b, 114c, 114d of sterile interface module 100. Moving floating plate 130 from the extended position to the compressed position facilitates a loading and/or unloading of electromechanical surgical instrument 60 onto/from sterile interface module 100 and helps prevent insertion contact/interference between drive transfer assemblies 114 of sterile interface module 100 and corresponding driven members 62a, 62b, 62c, etc. of electromechanical surgical instruments such as electromechanical surgical instrument 60.

Figure 5A:
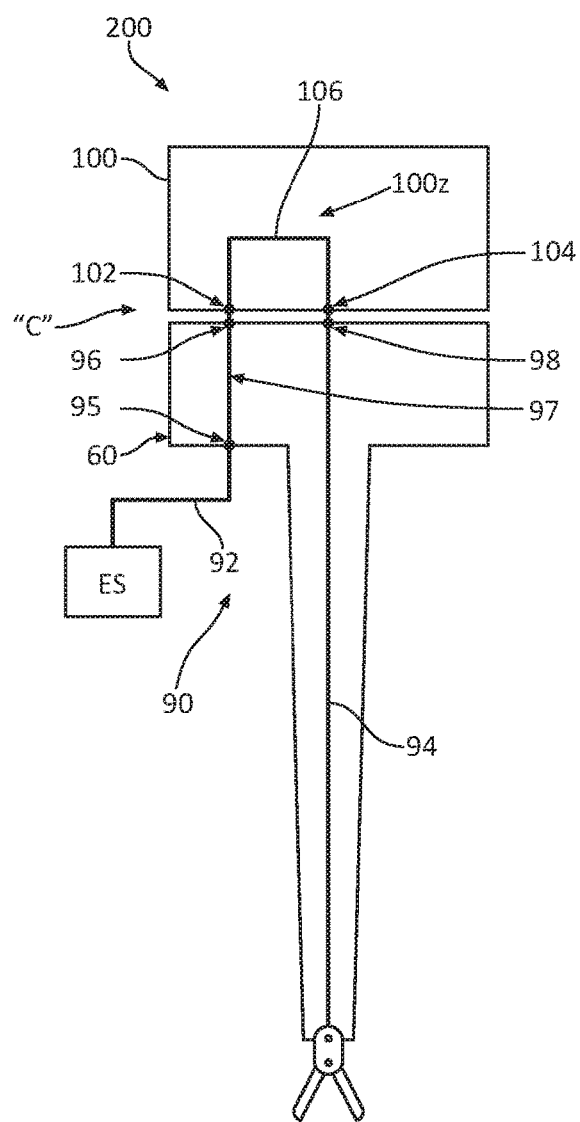
FIG. 5A is a side, elevational view illustrating the sterile interface module of FIG. 3 coupled to the electromechanical surgical instrument of FIG. 3.
Figure 5B:
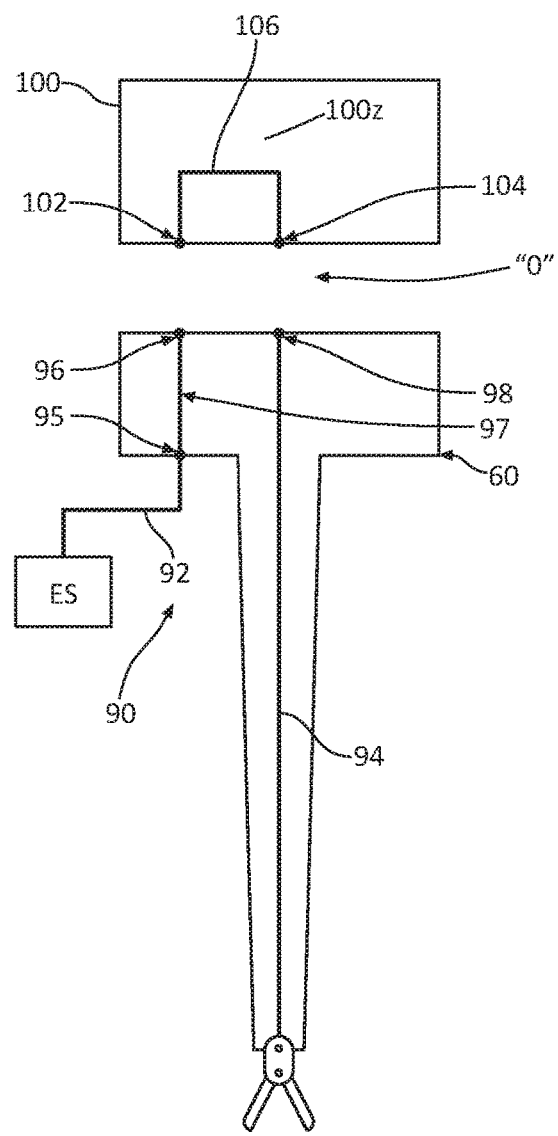
FIG. 5B is a side, elevational view illustrating the sterile interface module of FIG. 3 separated from the electromechanical surgical instrument of FIG. 3.

With reference to FIGS. 3, 5A, and 5B, body member 110 of sterile interface module 100 supports a jumper assembly 100z having a first electrical connector 102, a second electrical connector 104, and an electrical wiring 106 (e.g., one or more cables, wires, ribbons, jumpers, etc.) that extends between first and second electrical connectors 102, 104 to electrically couple first and second electrical connectors 102, 104 together. Jumper assembly 100z, or components thereof, may be positioned on upper portion 110a, intermediate portion 110b, and/or lower portion 110c of body member 110 of sterile interface module 100.

With reference to FIG. 2B, electromechanical surgical instrument 60 of robotic surgical system 1 generally includes one or more driven members 62a, 62b, 62c, etc. at a first end portion thereof that are coupled to one or more coupling members "CM" (e.g., cables, drive rods, etc.) extending along electromechanical surgical instrument 60 to end effector 60a of electromechanical surgical instrument 60 at a second end portion thereof. Driven members 62a, 62b, 62c, etc. are actuatable to manipulate the one or more coupling members "CM" for operating end effector 60a.

With reference to FIGS. 3, 5A, and 5B, electromechanical surgical instrument 60 includes an instrument electrical assembly 90 having an energy line 92 and an instrument line 94 that are electrically isolated from one another. Energy line 92 is coupled to electrosurgical energy source "ES" and includes a first electrical connector 95, a second electrical connector 96, and a second electrical wiring 97. Energy line 92 couples electrosurgical energy source "ES" to first electrical connector 95 and second electrical wiring 97 of energy line 92 couples first and second electrical connectors 95, 96 together. Instrument line 94 of electrical assembly 90 includes a third electrical connector 98 that electrically couples to one or more components of electromechanical surgical instrument 60, such as end effector 60a of the electromechanical surgical instrument 60.

Electromechanical surgical instrument 60, sterile interface module 100, and electrosurgical energy source "ES" of robotic surgical system 1 collectively define an energy disconnect system 200. Energy disconnect system 200 is configured to enable electromechanical surgical instrument 60 to become electrically active while coupled to electrosurgical energy source "ES" only upon attachment of electromechanical surgical instrument 60 to sterile interface module 100 of robotic surgical assembly 50. In particular, attachment of electromechanical surgical instrument 60 to sterile interface module 100 enables instrument electrical assembly 90 of electromechanical surgical instrument 60 to electrical couple to jumper assembly 100z of sterile interface module 100 so that electrical assembly 90 of electromechanical surgical instrument 60 and jumper assembly 100z of sterile interface module 100 create a continuous circuit in electrical communication with electrosurgical energy source "ES."

Energy disconnect system 200 is also configured such that if electromechanical surgical instrument 60 of energy disconnect system 200 is disconnected or otherwise removed from sterile interface module 100 of energy disconnect system 200, electromechanical surgical instrument 60 is prevented from receiving electrosurgical energy from electrosurgical energy source "ES" of energy disconnect system 200 so that electromechanical surgical instrument 60 cannot be inadvertently activated. In particular, removal or separation of electromechanical surgical instrument 60 from sterile interface module 100 enables instrument electrical assembly 90 of electromechanical surgical instrument 60 to electrical uncouple or electrically disconnect from jumper assembly 100z of sterile interface module 100 so that the continuous circuit formed by electrical assembly 90 of electromechanical surgical instrument 60 and jumper assembly 100z of sterile interface module 100 becomes electrically discontinuous and/or electrically isolated from electrosurgical energy source "ES."

In use, with reference to FIGS. 2A and 3, to couple an electromechanical surgical instrument, such as electromechanical surgical instrument 60, to sterile interface module 100, electromechanical surgical instrument 60 is transversely moved (e.g., side loaded) relative to the robotic surgical assembly 50 until electromechanical surgical instrument 60 is fully received or seated in lower portion 110c of sterile interface module 100 whereby energy disconnect system 200 enables the electromechanical surgical instrument 60 to become electrically active.

More specifically, when electromechanical surgical instrument 60 and sterile interface module 60 of robotic surgical assembly 50 are coupled to each other, second electrical connector 96 of electromechanical surgical instrument 60 is releasably connected to first electrical connector 102 of sterile interface module 100. Likewise, second electrical connector 104 of sterile interface module 100 is releasably connected to third electrical connector 98 of electromechanical surgical instrument 60. With respective second and third electrical connectors 96, 98 of electromechanical surgical instrument 60 connected to respective first and second electrical connectors 102, 104 of sterile interface module 100, a closed circuit "C" (FIG. 5A) is formed between electromechanical surgical instrument 60 and sterile interface module 100. Energy from electrosurgical energy source "ES" is routed through the closed circuit "C" to end effector 60a of electromechanical surgical instrument 60.

With robotic surgical assembly 50 of robotic surgical system 1 secured to one of surgical robotic arms 2, 3, of robotic surgical system 1, and electromechanical surgical instrument 60 of robotic surgical system 1 secured to sterile interface module 100 of robotic surgical system 1, a clinician can perform a surgical procedure by robotically controlling driven members 62a, 62b, 62c, etc. of electromechanical surgical instrument 60 with motor assembly 74 of robotic surgical assembly 50 as desired.

To remove electromechanical surgical instrument 60 from robotic surgical assembly 50, for example, to perform an instrument exchange, a clinician can depress paddles 64a, 64b of electromechanical surgical instrument 60 (FIG. 2A). Depression of the paddles 64a, 64b imparts a force on tabs 134a, 134b (FIG. 3) of the floating plate 130 of the sterile interface module 100 to move the floating plate 130 in a proximal direction relative to the body member 110 of sterile interface module 100. As the floating plate 130 moves in a proximal direction, drive transfer shafts 119 of respective drive transfer assemblies 114 translate with floating plate 130 of sterile interface module 100 in the proximal direction against biasing forces from springs (not shown) of respective drive transfer assemblies 114. Movement of drive transfer shafts 119 of respective drive transfer assemblies 114 relative to the body member 110 of sterile interface module 100 separates drive transfer shafts 119 of drive transfer assemblies 114 from respective driven members 62a, 62b, 62c, etc. of electromechanical surgical instrument 60. Once respective drive transfer assemblies 114 are separated from respective driven members 62a, 62b, 62c, etc. of electromechanical surgical instrument 60, electromechanical surgical instrument 60 can be slid laterally out from sterile interface module 100 to remove electromechanical surgical instrument 60 from sterile interface module 100.

When electromechanical surgical instrument 60 is disconnected, decoupled, or otherwise removed from sterile interface module 100 (FIG. 5B), electrical communication between electromechanical surgical instrument 60 and sterile interface module 100 ceases, and energy from the electrosurgical energy source "ES" is no longer provided to end effector 60a of electromechanical surgical instrument 60, even if the electrosurgical energy source "ES" is still powered on. Thus, disconnecting electromechanical surgical instrument 60 from sterile interface module 100 forms a broken or open circuit "O" (FIG. 5B).

Specifically, removing electromechanical surgical instrument 60 from sterile interface module 100 electrically disconnects second electrical connector 96 of electromechanical surgical instrument 60 from first electrical connector 102 of sterile interface module 100 and also disconnects second electrical connector 104 of sterile interface module 100 from third electrical connector 98 of electromechanical surgical instrument 60. Since second electrical connector 96 and third electrical connector 98 of electromechanical surgical instrument 60 are separated or otherwise electrically isolated from each other, electromechanical surgical instrument 60 cannot activate unless connected to sterile interface module 100. More specifically, electromechanical surgical instrument 60 relies on first electrical connector 102 and second electrical connector 104 of sterile interface module 100 to complete the closed circuit "C" (FIG. 5A) and send power from electrosurgical energy source "ES" to end effector 60a of electromechanical surgical instrument 60.

To reestablish the electrical connection (and the closed circuit "C") between electromechanical surgical instrument 60 and sterile interface module 100, electromechanical surgical instrument 60 can be reattached to sterile interface module 100. Alternatively, a different electromechanical surgical instrument can be attached to the sterile interface module 100.

With reference to FIGS. 6A and 6B, provided in accordance with another embodiment of the present disclosure, is a sterile interface module 300. Sterile interface module 300 may be configured for use with robotic surgical assembly 50, an electromechanical surgical instrument such as electromechanical surgical instrument 60, and/or instrument drive unit 70. Sterile interface module 300 may be substantially similar to the sterile interface module 100 described above, except as described herein.

Sterile interface module 300 generally includes a floating plate 310 having a first electrical connector 311 and a second electrical connector 312 that are joined by an electrical wiring 313 to form a jumper assembly 310a. First and second electrical connectors 311, 312 and electrical wiring 313 may be disposed directly on (or in) a surface of floating plate 310. The first and second electrical connectors 311, 312 of floating plate 310 of sterile interface module 300 may be configured to releasably connect, e.g., to respective electrical connectors 96, 98 of electromechanical surgical instrument 60.

In use, as floating plate 310 moves in a proximal direction, electrical connectors 311, 312 of floating plate 310 of sterile interface module 300 are configured to electrically disconnect and/or uncouple from corresponding electrical connectors of an electromechanical surgical instrument, such as electrical connectors 96, 98 of electromechanical surgical instrument 60.

In embodiments, any of the electrical connectors described herein may be electrodes, terminals, contacts, plugs, pogo pins, combinations or variations thereof, or the like. Likewise, any of the electrical wirings described herein may be cables, conductors, wires, jumpers, combinations or variations thereof, or the like. As can be appreciated, any number of electrical connectors, electrical wirings, or combinations or variations thereof, may be used.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

The invention claimed is:

1. A robotic surgical system, comprising:
an electrosurgical energy source;
an instrument drive unit supporting a motor assembly;

a sterile interface module supporting a drive transfer assembly coupled to the motor assembly of the instrument drive unit, the sterile interface module having an electrical jumper assembly, the electrical jumper assembly including first and second electrical connectors and an electrical wiring that connects the first and second electrical connectors together; and a robotic surgical instrument defining a longitudinal axis and having an end effector, the robotic surgical instrument supporting a driven member assembly selectively coupled to the drive transfer assembly of the sterile interface module such that longitudinal axes about which the motor assembly, the drive transfer assembly, and the driven member assembly rotate extend in the same direction as the longitudinal axis of the robotic surgical instrument, the robotic surgical instrument disposed in electrical communication with the electrosurgical energy source while the robotic surgical instrument is coupled to the sterile interface module such that the electrical wiring of the sterile interface module transmits electrical energy from the first electrical connector to the second electrical connector to energize the end effector of the robotic surgical instrument, the robotic surgical instrument configured to remain connected to the electrosurgical energy source and automatically electrically disconnect the end effector from the electrosurgical energy source and the electrical jumper assembly to deenergize the end effector when the robotic surgical instrument is uncoupled from the sterile interface module.

2. The robotic surgical system according to claim 1, wherein the robotic surgical instrument includes a first electrical connector coupled to the electrosurgical energy source and configured to electrically couple to the electrical jumper assembly of the sterile interface module.

3. The robotic surgical system according to claim 2, wherein the robotic surgical instrument includes a second electrical connector in electrical communication with the end effector of the robotic surgical instrument, the first and second electrical connectors of the robotic surgical instrument electrically isolated from each other when the robotic surgical instrument is uncoupled from the sterile interface module.

4. The robotic surgical system according to claim 3, wherein an electrical wiring couples the second electrical connector of the robotic surgical instrument to the end effector.

5. The robotic surgical system according to claim 3, wherein the first and second electrical connectors of the sterile interface module are configured for electrical communication with the first and second electrical connectors of the robotic surgical instrument.

6. The robotic surgical system according to claim 5, wherein when the robotic surgical instrument is coupled to the sterile interface module, the first and second electrical connectors of the robotic surgical instrument are in electrical communication with the first and second electrical connectors of the sterile interface module such that the robotic surgical instrument and the sterile interface module form a closed circuit with the electrical jumper assembly.

7. The robotic surgical system of claim 5, wherein when the robotic surgical instrument is uncoupled from the sterile interface module, the first and second electrical connectors of the robotic surgical instrument are electrically isolated from the first and second electrical connectors of the sterile interface module.

8. The robotic surgical system according to claim 3, wherein the robotic surgical instrument further includes a third electrical connector in electrical communication with the electrosurgical energy source and the first electrical connector of the robotic surgical instrument.

9. The robotic surgical system according to claim 2, wherein the first electrical connector of the robotic surgical instrument is a pogo pin.

10. A robotic surgical system, comprising:
an electrosurgical energy source;
an instrument drive unit supporting a motor assembly;
a sterile interface module supporting a drive transfer assembly coupled to the motor assembly of the instrument drive unit and including a first electrical connector and a second electrical connector, the first and second electrical connectors being electrically connected by opposite ends of an electrical wiring; and
a robotic surgical instrument defining a longitudinal axis and having an end effector, the robotic surgical instrument supporting a driven member assembly and including a first electrical connector, the driven member assembly selectively coupled to the drive transfer assembly of the sterile interface module such that the drive transfer assembly is disposed longitudinally between the motor assembly and the driven member assembly to couple the motor assembly and the driven member assembly together and to transfer rotational force from the motor assembly to the driven member assembly, the first electrical connector of the robotic surgical instrument configured to couple to the first electrical connector of the sterile interface module when the robotic surgical instrument is coupled to the sterile interface module, the robotic surgical instrument disposed in electrical communication with the electrosurgical energy source while the first electrical connector of the robotic surgical instrument is coupled to the first electrical connector of the sterile interface module, the electrical wiring of the sterile interface module configured to transmit electrical energy from the first electrical connector to the second electrical connector to energize the end effector of the robotic surgical instrument when the sterile interface module is coupled to the robotic surgical instrument, the robotic surgical instrument configured to remain connected to the electrosurgical energy source and electrically disconnect the end effector from the electrosurgical energy source and the first and second electrical connectors of the sterile interface module to deenergize the end effector when the robotic surgical instrument is uncoupled from the sterile interface module.

11. The robotic surgical system according to claim 10, wherein the first electrical connector of the robotic surgical instrument is coupled to the electrosurgical energy source, the robotic surgical instrument including a second electrical connector in electrical communication with the end effector of the robotic surgical instrument, the first and second electrical connectors of the robotic surgical instrument electrically isolated from each other when the robotic surgical instrument is uncoupled from the sterile interface module.

12. The robotic surgical system according to claim 11, wherein an electrical wiring couples the second electrical connector of the robotic surgical instrument to the end effector.

13. The robotic surgical system according to claim 11, further comprising a floating plate disposed within the sterile interface module, the floating plate supporting the first and second electrical connectors and the electrical wiring of the sterile interface module, the floating plate configured to move from a first position to a second position within the sterile interface module, wherein when the floating plate moves from the first position to the second position, the first and second electrical connectors of the sterile interface module electrically disconnect from the first and second electrical connectors of the robotic surgical instrument.

14. The robotic surgical system according to claim 11, wherein when the robotic surgical instrument is coupled to the sterile interface module, the first and second electrical connectors of the robotic surgical instrument are in electrical communication with the first and second electrical connectors of the sterile interface module such that the robotic surgical instrument and the sterile interface module form a closed circuit.

15. The robotic surgical system according to claim 10, wherein at least one of the first or second electrical connectors of the sterile interface module are pogo pins.

16. A method for selectively electrically activating a robotic surgical instrument defining a longitudinal axis and having an end effector, the method comprising:
- coupling the robotic surgical instrument to an electrosurgical energy source;
- loading the robotic surgical instrument onto a sterile interface module while the robotic surgical instrument is coupled to the electrosurgical energy source such that a motor assembly is configured to impart rotational force to a drive transfer assembly of the sterile interface module that extends longitudinally from the motor assembly, and the drive transfer assembly is configured to impart rotational force to a driven member assembly of the robotic surgical instrument that extends longitudinally from the drive transfer assembly;
- electrically coupling a jumper assembly of the sterile interface module to at least one electrical component of the robotic surgical instrument to enable electrosurgical energy to be conducted through the robotic surgical instrument and the sterile interface module upon loading the robotic surgical instrument onto the sterile interface module for energizing the end effector, wherein the jumper assembly includes first and second electrical connectors and an electrical wiring that connects the first and second electrical connectors together to transmit electrical energy from the first electrical connector, through the sterile interface module, to the second electrical connector to energize the end effector of the robotic surgical instrument when the sterile interface module is coupled to the robotic surgical instrument; and
- selectively unloading the robotic surgical instrument from the sterile interface module to automatically deenergize the end effector of the robotic surgical instrument such that the robotic surgical instrument remains coupled to the electrosurgical energy source without the end effector being energized after the robotic surgical instrument is unloaded from the sterile interface module.

* * * * *